United States Patent
Jacobson

(10) Patent No.: US 9,358,400 B2
(45) Date of Patent: *Jun. 7, 2016

(54) LEADLESS CARDIAC PACEMAKER

(75) Inventor: Peter M. Jacobson, Chanhassen, MN (US)

(73) Assignee: Pacesetter, Inc., Sunnyvale, CA (US)

( * ) Notice: Subject to any disclaimer, the term of this patent is extended or adjusted under 35 U.S.C. 154(b) by 1300 days.

This patent is subject to a terminal disclaimer.

(21) Appl. No.: 11/549,581

(22) Filed: Oct. 13, 2006

(65) Prior Publication Data

US 2007/0088396 A1    Apr. 19, 2007

Related U.S. Application Data

(60) Provisional application No. 60/726,706, filed on Oct. 14, 2005, provisional application No. 60/729,671, filed on Oct. 24, 2005, provisional application No. 60/737,296, filed on Nov. 16, 2005, provisional application No. 60/739,901, filed on Nov. 26, 2005, provisional application No. 60/749,017, filed on Dec. 10, 2005, provisional application No. 60/761,531, filed on Jan. 24, 2006, provisional application No. 60/761,740, filed on Jan. 24, 2006.

(51) Int. Cl.
*A61N 1/39*    (2006.01)
*A61N 1/05*    (2006.01)
(Continued)

(52) U.S. Cl.
CPC .............. *A61N 1/3962* (2013.01); *A61N 1/056* (2013.01); *A61N 1/0587* (2013.01); *A61N 1/368* (2013.01); *A61N 1/3621* (2013.01); *A61N 1/3627* (2013.01); *A61N 1/36514* (2013.01); *A61N 1/372* (2013.01); *A61N 1/3704* (2013.01); *A61N 1/375* (2013.01); *A61N 1/3706* (2013.01); *A61N 1/3727* (2013.01); *A61N 1/3756* (2013.01); *A61N 1/37217* (2013.01); *A61N 1/37288* (2013.01); *A61N 1/3925* (2013.01); *A61N 1/3956* (2013.01); *H04B 13/005* (2013.01); *A61M 25/0662* (2013.01);
(Continued)

(58) Field of Classification Search
CPC ....... A61N 1/05; A61N 1/056; A61N 1/0587; A61N 1/36; A61N 1/3621; A61N 1/3627; A61N 1/368; A61N 1/372; A61N 1/3725; A61N 1/3962; A61N 1/3756
USPC ........ 607/9, 27, 32, 119, 122, 2, 28; 600/373, 600/374
See application file for complete search history.

(56) References Cited

U.S. PATENT DOCUMENTS 3,199,508 A    8/1965  Roth
3,212,496 A    10/1965 Preston
(Continued)

FOREIGN PATENT DOCUMENTS

EP    0362611 A1    4/1990
EP    1115329 A2    7/2001
(Continued)

OTHER PUBLICATIONS

U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. No. 7,630,767).
(Continued)

*Primary Examiner* — Christopher A Flory
(74) *Attorney, Agent, or Firm* — Theresa A. Raymer

(57) ABSTRACT

In a cardiac pacing system, a leadless cardiac pacemaker is configured for implantation in electrical contact with a cardiac chamber and configured for leadless pacing.

29 Claims, 5 Drawing Sheets

(51) Int. Cl.
  *A61N 1/36* (2006.01)
  *A61N 1/375* (2006.01)
  *A61N 1/362* (2006.01)
  *A61N 1/365* (2006.01)
  *A61N 1/368* (2006.01)
  *A61N 1/372* (2006.01)
  *H04B 13/00* (2006.01)
  *A61N 1/37* (2006.01)
  *A61M 25/06* (2006.01)

(52) U.S. Cl.
  CPC .......... *A61N 1/3684* (2013.01); *A61N 1/36542* (2013.01); *A61N 1/37205* (2013.01); *A61N 1/37252* (2013.01); *A61N 2001/058* (2013.01)

(56) References Cited

U.S. PATENT DOCUMENTS

| | | |
|---|---|---|
| 3,218,638 A | 11/1965 | Honig |
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,836,798 A * | 9/1974 | Greatbatch ................ 310/303 |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson et al. |
| 3,943,926 A | 3/1976 | Arvizu Barragan |
| 3,943,936 A | 3/1976 | Rasor et al. |
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,087,389 A | 5/1978 | Coppola |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| RE30,366 E | 8/1980 | Rasor et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,312,354 A | 1/1982 | Walters |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,458,692 A | 7/1984 | Simson |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey, III et al. |
| 4,817,605 A * | 4/1989 | Sholder ................ A61N 1/368 607/28 |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,858,610 A | 8/1989 | Callaghan et al. |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder |
| 4,987,897 A | 1/1991 | Funke |
| 4,995,390 A | 2/1991 | Cook et al. |
| 5,010,887 A | 4/1991 | Thornander |
| 5,012,806 A | 5/1991 | De Bellis |
| 5,014,700 A | 5/1991 | Alt |
| 5,014,701 A | 5/1991 | Pless et al. |
| 5,031,615 A | 7/1991 | Alt |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A | 2/1993 | Weiss |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,247,945 A | 9/1993 | Heinze et al. |
| 5,259,394 A | 11/1993 | Bens |
| 5,260,621 A | 11/1993 | Little et al. |
| 5,267,150 A | 11/1993 | Wilkinson |

(56) References Cited

U.S. PATENT DOCUMENTS

| | | | |
|---|---|---|---|
| 5,282,841 A | 2/1994 | Szyszkowski | |
| 5,284,136 A | 2/1994 | Hauck et al. | |
| 5,291,902 A | 3/1994 | Carman | |
| 5,300,093 A | 4/1994 | Koestner et al. | |
| 5,304,206 A | 4/1994 | Baker, Jr. et al. | |
| 5,304,209 A | 4/1994 | Adams et al. | |
| 5,313,953 A | 5/1994 | Yomtov et al. | |
| 5,318,596 A | 6/1994 | Barreras et al. | |
| 5,324,316 A | 6/1994 | Schulman et al. | |
| 5,331,966 A | 7/1994 | Bennett et al. | |
| 5,333,095 A | 7/1994 | Stevenson et al. | |
| 5,336,244 A | 8/1994 | Weijand | |
| 5,342,401 A | 8/1994 | Spano et al. | |
| 5,354,317 A | 10/1994 | Alt | |
| 5,358,514 A | 10/1994 | Schulman et al. | |
| 5,373,852 A | 12/1994 | Harrison et al. | |
| 5,383,912 A | 1/1995 | Cox et al. | |
| 5,383,915 A | 1/1995 | Adams | |
| 5,404,877 A | 4/1995 | Nolan et al. | |
| 5,405,367 A | 4/1995 | Schulman et al. | |
| 5,406,444 A | 4/1995 | Selfried et al. | |
| 5,411,532 A | 5/1995 | Mortazavi | |
| 5,411,535 A | 5/1995 | Fuji et al. | |
| 5,411,537 A | 5/1995 | Munshi et al. | |
| 5,417,222 A | 5/1995 | Dempsey et al. | |
| 5,419,337 A | 5/1995 | Dempsey et al. | |
| 5,431,171 A | 7/1995 | Harrison et al. | |
| 5,446,447 A | 8/1995 | Carney et al. | |
| 5,456,261 A | 10/1995 | Luczyk | |
| 5,466,246 A | 11/1995 | Silvian | |
| 5,469,857 A | 11/1995 | Laurent et al. | |
| 5,480,415 A | 1/1996 | Cox et al. | |
| 5,481,262 A | 1/1996 | Urbas et al. | |
| 5,522,876 A | 6/1996 | Rusink | |
| 5,531,779 A | 7/1996 | Dahl et al. | |
| 5,531,781 A | 7/1996 | Alferness et al. | |
| 5,531,783 A | 7/1996 | Giele et al. | |
| 5,539,775 A | 7/1996 | Tuttle et al. | |
| 5,549,654 A | 8/1996 | Powell | |
| 5,549,659 A | 8/1996 | Johansen et al. | |
| 5,551,427 A | 9/1996 | Altman | |
| 5,556,421 A | 9/1996 | Prutchi et al. | |
| 5,562,717 A | 10/1996 | Tippey et al. | |
| 5,571,143 A | 11/1996 | Hoegnelid et al. | |
| 5,571,148 A | 11/1996 | Loeb et al. | |
| 5,579,775 A | 12/1996 | Dempsey et al. | |
| 5,586,556 A | 12/1996 | Spivey et al. | |
| 5,591,217 A | 1/1997 | Barreras | |
| 5,598,848 A | 2/1997 | Swanson et al. | |
| 5,649,952 A | 7/1997 | Lam | |
| 5,650,759 A | 7/1997 | Hittman et al. | |
| 5,654,984 A | 8/1997 | Hershbarger et al. | |
| 5,662,689 A | 9/1997 | Elsberry et al. | |
| 5,669,391 A | 9/1997 | Williams | |
| 5,674,259 A | 10/1997 | Gray | |
| 5,676,153 A | 10/1997 | Smith et al. | |
| 5,693,076 A | 12/1997 | Kaemmerer | |
| 5,694,940 A | 12/1997 | Unger et al. | |
| 5,694,952 A | 12/1997 | Lidman et al. | |
| 5,697,958 A | 12/1997 | Paul et al. | |
| 5,702,427 A | 12/1997 | Ecker et al. | |
| 5,725,559 A | 3/1998 | Alt et al. | |
| 5,728,154 A | 3/1998 | Crossett et al. | |
| 5,730,143 A | 3/1998 | Schwarzberg | |
| 5,735,880 A * | 4/1998 | Prutchi et al. | 607/9 |
| 5,738,102 A | 4/1998 | Lemelson | |
| 5,740,811 A | 4/1998 | Hedberg et al. | |
| 5,741,314 A | 4/1998 | Daly et al. | |
| 5,766,231 A | 6/1998 | Erickson et al. | |
| 5,792,202 A | 8/1998 | Rueter | |
| 5,792,205 A | 8/1998 | Alt et al. | |
| 5,792,208 A | 8/1998 | Gray | |
| 5,810,735 A | 9/1998 | Halperin et al. | |
| 5,814,076 A | 9/1998 | Brownlee | |
| 5,814,087 A | 9/1998 | Renirie | |
| 5,814,089 A | 9/1998 | Stokes et al. | |
| 5,824,016 A | 10/1998 | Ekwall | |
| 5,871,451 A | 2/1999 | Unger et al. | |
| 5,876,353 A | 3/1999 | Riff | |
| 5,876,425 A | 3/1999 | Gord et al. | |
| 5,891,178 A | 4/1999 | Mann et al. | |
| 5,899,928 A | 5/1999 | Sholder et al. | |
| 5,935,079 A | 8/1999 | Swanson et al. | |
| 5,954,761 A | 9/1999 | Machek et al. | |
| 5,957,861 A | 9/1999 | Combs et al. | |
| 5,984,861 A | 11/1999 | Crowley | |
| 5,987,352 A | 11/1999 | Klein et al. | |
| 5,995,876 A | 11/1999 | Kruse et al. | |
| 5,999,857 A | 12/1999 | Weijand et al. | |
| 6,002,969 A | 12/1999 | Machek et al. | |
| 6,004,269 A | 12/1999 | Crowley et al. | |
| 6,061,596 A | 5/2000 | Richmond et al. | |
| 6,076,016 A | 6/2000 | Feierbach | |
| 6,080,187 A | 6/2000 | Alt et al. | |
| 6,093,146 A | 7/2000 | Filangeri | |
| 6,096,065 A | 8/2000 | Crowley | |
| 6,102,874 A | 8/2000 | Stone et al. | |
| 6,112,116 A | 8/2000 | Fischell et al. | |
| 6,112,119 A * | 8/2000 | Schuelke | A61N 1/3704 607/9 |
| 6,115,628 A | 9/2000 | Stadler et al. | |
| 6,115,630 A | 9/2000 | Stadler et al. | |
| 6,115,636 A | 9/2000 | Ryan | |
| 6,119,031 A | 9/2000 | Crowley | |
| 6,125,290 A | 9/2000 | Miesel | |
| 6,125,291 A | 9/2000 | Miesel et al. | |
| 6,128,526 A | 10/2000 | Stadler et al. | |
| 6,129,751 A | 10/2000 | Lucchesi et al. | |
| 6,132,390 A | 10/2000 | Cookston et al. | |
| 6,132,456 A | 10/2000 | Sommer et al. | |
| 6,134,459 A | 10/2000 | Roberts et al. | |
| 6,134,470 A | 10/2000 | Hartlaub | |
| 6,139,510 A | 10/2000 | Palermo | |
| 6,141,584 A | 10/2000 | Rockwell et al. | |
| 6,141,588 A | 10/2000 | Cox et al. | |
| 6,141,592 A | 10/2000 | Pauly | |
| 6,144,866 A | 11/2000 | Miesel et al. | |
| 6,148,230 A | 11/2000 | KenKnight | |
| 6,152,882 A | 11/2000 | Prutchi | |
| 6,163,723 A | 12/2000 | Roberts et al. | |
| 6,164,284 A | 12/2000 | Schulman et al. | |
| 6,167,310 A | 12/2000 | Grevious | |
| 6,178,349 B1 | 1/2001 | Kieval | |
| 6,178,356 B1 | 1/2001 | Chastain et al. | |
| 6,185,443 B1 | 2/2001 | Crowley | |
| 6,185,452 B1 | 2/2001 | Schulman et al. | |
| 6,185,464 B1 | 2/2001 | Bonner et al. | |
| 6,188,932 B1 | 2/2001 | Lindegren | |
| 6,190,324 B1 | 2/2001 | Kieval et al. | |
| 6,198,952 B1 | 3/2001 | Miesel | |
| 6,201,993 B1 | 3/2001 | Kruse et al. | |
| 6,208,894 B1 | 3/2001 | Schulman et al. | |
| 6,208,900 B1 | 3/2001 | Ecker et al. | |
| 6,223,081 B1 | 4/2001 | Kerver | |
| 6,230,059 B1 | 5/2001 | Duffin | |
| 6,236,882 B1 | 5/2001 | Lee et al. | |
| 6,240,321 B1 | 5/2001 | Janke et al. | |
| 6,243,608 B1 | 6/2001 | Pauly et al. | |
| 6,248,080 B1 | 6/2001 | Miesel et al. | |
| 6,263,245 B1 | 7/2001 | Snell | |
| 6,265,100 B1 | 7/2001 | Saaski et al. | |
| 6,266,554 B1 | 7/2001 | Hsu et al. | |
| 6,266,564 B1 | 7/2001 | Hill et al. | |
| 6,272,379 B1 | 8/2001 | Fischell et al. | |
| 6,280,409 B1 | 8/2001 | Stone et al. | |
| 6,289,229 B1 | 9/2001 | Crowley | |
| 6,306,088 B1 | 10/2001 | Krausman et al. | |
| 6,310,960 B1 | 10/2001 | Saaski et al. | |
| 6,315,721 B2 | 11/2001 | Schulman et al. | |
| 6,324,418 B1 | 11/2001 | Crowley et al. | |
| 6,324,421 B1 | 11/2001 | Stadler et al. | |
| RE37,463 E | 12/2001 | Altman | |
| 6,343,227 B1 | 1/2002 | Crowley | |
| 6,343,233 B1 | 1/2002 | Werner et al. | |

(56) References Cited

U.S. PATENT DOCUMENTS

| | | |
|---|---|---|
| 6,347,245 B1 | 2/2002 | Lee et al. |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott |
| 6,482,154 B1 | 11/2002 | Haubrich et al. |
| 6,484,055 B1 | 11/2002 | Marcovecchio |
| 6,484,057 B2 | 11/2002 | Ideker et al. |
| 6,490,487 B1 | 12/2002 | Kraus et al. |
| 6,496,715 B1 * | 12/2002 | Lee et al. ............... 600/424 |
| 6,498,951 B1 | 12/2002 | Larson et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | KenKnight |
| 6,542,781 B1 | 4/2003 | Koblish et al. |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 | 6/2003 | Haupert et al. |
| 6,584,351 B1 | 6/2003 | Ekwall |
| 6,584,352 B2 | 6/2003 | Combs et al. |
| 6,589,187 B1 | 7/2003 | Dirnberger et al. |
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,697,677 B2 | 2/2004 | Dahl et al. |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,716,238 B2 | 4/2004 | Elliott |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,728,576 B2 | 4/2004 | Thompson et al. |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,856,835 B2 | 2/2005 | Bardy et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |

(56) References Cited

U.S. PATENT DOCUMENTS

| | | |
|---|---|---|
| 6,931,327 B2 | 8/2005 | Goode, Jr. et al. |
| 6,999,821 B2 | 2/2006 | Jenney et al. |
| 7,001,372 B2 | 2/2006 | Richter |
| 7,023,359 B2 | 4/2006 | Goetz et al. |
| 7,027,876 B2 | 4/2006 | Casavant et al. |
| 7,146,222 B2 | 12/2006 | Boling |
| 7,146,225 B2 | 12/2006 | Guenst et al. |
| 7,164,950 B2 | 1/2007 | Kroll et al. |
| 7,181,505 B2 | 2/2007 | Haller et al. |
| 7,187,971 B2 | 3/2007 | Sommer et al. |
| 7,200,437 B1 | 4/2007 | Nabutovsky et al. |
| 7,212,870 B1 | 5/2007 | Helland |
| 7,277,754 B2 | 10/2007 | McCabe et al. |
| 7,289,853 B1 | 10/2007 | Campbell et al. |
| 7,307,544 B2 | 12/2007 | Kim et al. |
| 7,363,090 B2 | 4/2008 | Halperin et al. |
| 7,532,933 B2 | 5/2009 | Hastings et al. |
| 7,558,631 B2 | 7/2009 | Cowan et al. |
| 7,565,195 B1 * | 7/2009 | Kroll et al. .................. 607/2 |
| 7,616,991 B2 | 11/2009 | Mann et al. |
| 7,630,767 B1 | 12/2009 | Poore et al. |
| 7,634,313 B1 | 12/2009 | Kroll et al. |
| 7,650,186 B2 | 1/2010 | Hastings et al. |
| 7,848,823 B2 | 12/2010 | Drasler et al. |
| 7,937,148 B2 | 5/2011 | Jacobson |
| 7,945,333 B2 | 5/2011 | Jacobson |
| 8,010,209 B2 | 8/2011 | Jacobson |
| 8,295,939 B2 | 10/2012 | Jacobson |
| 8,352,025 B2 | 1/2013 | Jacobson |
| 8,457,742 B2 | 6/2013 | Jacobson |
| 8,788,053 B2 | 7/2014 | Jacobson |
| 9,072,913 B2 * | 7/2015 | Jacobson ............. A61N 1/3925 |
| 9,216,298 B2 * | 12/2015 | Jacobson ............. A61N 1/3925 |
| 2001/0031999 A1 * | 10/2001 | Carter et al. ................... 607/69 |
| 2002/0032467 A1 | 3/2002 | Shemer et al. |
| 2002/0077686 A1 | 6/2002 | Westlund et al. |
| 2002/0099423 A1 | 7/2002 | Berg et al. |
| 2002/0099430 A1 | 7/2002 | Verness |
| 2002/0111662 A1 | 8/2002 | Iaizzo et al. |
| 2002/0116028 A1 | 8/2002 | Greatbatch et al. |
| 2002/0147488 A1 | 10/2002 | Doan et al. |
| 2003/0040666 A1 | 2/2003 | Rutten et al. |
| 2003/0141995 A1 | 7/2003 | Lin |
| 2003/0158584 A1 | 8/2003 | Cates et al. |
| 2003/0163184 A1 | 8/2003 | Scheiner |
| 2003/0199941 A1 | 10/2003 | Nielsen et al. |
| 2004/0011366 A1 | 1/2004 | Schulman et al. |
| 2004/0059392 A1 | 3/2004 | Parramon et al. |
| 2004/0116939 A1 | 6/2004 | Goode |
| 2004/0133242 A1 | 7/2004 | Chapman et al. |
| 2004/0143262 A1 | 7/2004 | Visram et al. |
| 2004/0147973 A1 | 7/2004 | Hauser |
| 2004/0167587 A1 | 8/2004 | Thompson |
| 2004/0172116 A1 | 9/2004 | Seifert et al. |
| 2004/0193223 A1 | 9/2004 | Kramer et al. |
| 2004/0249417 A1 | 12/2004 | Ransbury et al. |
| 2004/0260349 A1 | 12/2004 | Stroebel |
| 2005/0038474 A1 | 2/2005 | Wool |
| 2005/0038491 A1 | 2/2005 | Haack |
| 2005/0043765 A1 | 2/2005 | Williams et al. |
| 2005/0075682 A1 | 4/2005 | Schulman et al. |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0105613 A1 | 5/2006 | Carroll |
| 2006/0108335 A1 | 5/2006 | Zhao et al. |
| 2006/0121475 A1 | 6/2006 | Davids et al. |
| 2006/0135999 A1 | 6/2006 | Bodner et al. |
| 2006/0136004 A1 | 6/2006 | Cowan et al. |
| 2006/0161222 A1 | 7/2006 | Haubrich et al. |
| 2006/0241705 A1 | 10/2006 | Neumann et al. |
| 2006/0247750 A1 | 11/2006 | Seifert et al. |
| 2006/0282150 A1 | 12/2006 | Olson et al. |
| 2006/0287691 A1 * | 12/2006 | Drew .................. A61B 5/0006 607/59 |
| 2007/0016263 A1 | 1/2007 | Armstrong et al. |
| 2007/0043414 A1 | 2/2007 | Fifer et al. |
| 2007/0055184 A1 | 3/2007 | Echt et al. |
| 2007/0088394 A1 | 4/2007 | Jacobson |
| 2007/0088397 A1 | 4/2007 | Jacobson |
| 2007/0088398 A1 | 4/2007 | Jacobson |
| 2007/0088400 A1 | 4/2007 | Jacobson |
| 2007/0088405 A1 | 4/2007 | Jacobson |
| 2007/0088418 A1 | 4/2007 | Jacobson |
| 2007/0123923 A1 | 5/2007 | Lindstrom et al. |
| 2007/0142709 A1 | 6/2007 | Martone et al. |
| 2007/0167994 A1 | 7/2007 | Shelton et al. |
| 2007/0179552 A1 | 8/2007 | Dennis et al. |
| 2007/0270675 A1 | 11/2007 | Kane et al. |
| 2007/0276004 A1 | 11/2007 | Hirsch et al. |
| 2007/0276444 A1 | 11/2007 | Gelbart et al. |
| 2007/0293904 A1 | 12/2007 | Gelbart et al. |
| 2008/0004535 A1 | 1/2008 | Smits |
| 2008/0021532 A1 | 1/2008 | Kveen et al. |
| 2008/0039738 A1 | 2/2008 | Dinsmoor et al. |
| 2008/0086168 A1 | 4/2008 | Cahill |
| 2008/0091255 A1 | 4/2008 | Caparso et al. |
| 2008/0119911 A1 | 5/2008 | Rosero |
| 2008/0243218 A1 | 10/2008 | Bottomley et al. |
| 2008/0269591 A1 | 10/2008 | Halperin et al. |
| 2008/0306359 A1 | 12/2008 | Zdeblick et al. |
| 2009/0018599 A1 | 1/2009 | Hastings et al. |
| 2009/0082827 A1 | 3/2009 | Kveen et al. |
| 2009/0082828 A1 | 3/2009 | Ostroff |
| 2009/0149902 A1 | 6/2009 | Kumar et al. |
| 2009/0171408 A1 | 7/2009 | Solem |
| 2010/0069983 A1 | 3/2010 | Peacock, III et al. |
| 2010/0198288 A1 | 8/2010 | Ostroff |
| 2010/0249828 A1 | 9/2010 | Mavani et al. |
| 2010/0292541 A1 | 11/2010 | Hashiba et al. |
| 2010/0305653 A1 | 12/2010 | Lund et al. |
| 2010/0305656 A1 | 12/2010 | Imran et al. |
| 2010/0312332 A1 | 12/2010 | Forster et al. |
| 2011/0004117 A1 | 1/2011 | Neville et al. |
| 2011/0071586 A1 | 3/2011 | Jacobson |
| 2011/0077708 A1 | 3/2011 | Ostroff |
| 2011/0184492 A1 | 7/2011 | Martens et al. |
| 2011/0208260 A1 | 8/2011 | Jacobson |
| 2011/0218587 A1 | 9/2011 | Jacobson |
| 2011/0282423 A1 | 11/2011 | Jacobson |
| 2012/0089198 A1 | 4/2012 | Ostroff |
| 2012/0095539 A1 | 4/2012 | Khairkhahan et al. |
| 2012/0109236 A1 | 5/2012 | Jacobson et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0197373 A1 | 8/2012 | Khairkhahan et al. |
| 2013/0041422 A1 | 2/2013 | Jacobson |
| 2013/0103109 A1 | 4/2013 | Jacobson |
| 2013/0123875 A1 | 5/2013 | Varady et al. |
| 2014/0051965 A1 | 2/2014 | Zdeblick et al. |

FOREIGN PATENT DOCUMENTS

| | | |
|---|---|---|
| EP | 1741465 A1 | 1/2007 |
| JP | H04506167 A | 10/1992 |
| JP | 05-245215 | 9/1993 |
| JP | 06/507096 | 3/2006 |
| JP | 06/516449 | 7/2006 |
| JP | 2006526483 A | 11/2006 |
| WO | WO-9312714 A1 | 7/1993 |
| WO | WO 98/37926 A1 | 9/1998 |
| WO | WO-0234333 A2 | 5/2002 |
| WO | WO2004/012811 | 2/2004 |
| WO | WO 2006/065394 A1 | 6/2006 |
| WO | WO 2007/047681 A2 | 4/2007 |

(56) References Cited

FOREIGN PATENT DOCUMENTS

| WO | WO 2007/059386 A2 | 5/2007 |
|---|---|---|
| WO | WO-2008058265 A2 | 5/2008 |
| WO | WO-2010/013170 A1 | 2/2010 |

OTHER PUBLICATIONS

Beeby et al.; Micromachined silicon generator for harvesting power from vibrations; (Proceedings) PowerMEMS 2004; Kyoto, Japan; pp. 104-107; Nov. 28-30, 2004.
Bordacher et al.; Impact and prevention of far-field sensing in fallback mode switches; PACE; vol. 26 (pt. II); pp. 206-209; Jan. 2003.
Brandt et al.; Far-field QRS complex sensing: prevalence and timing with bipolar atrial leads; PACE; vol. 23; pp. 315-320; Mar. 2000.
Brown, Eric S.; The atomic battery; Technology Review: Published by MIT; 4 pgs.; Jun. 16, 2005.
Irnich et al.; Do we need pacemakers resistant to magnetic resonance imaging; Europace; vol. 7; pp. 353-365; Feb. 20025.
Irnich; Electronic security systems and active implantable medical devices; Journal of PACE; vol. 25; No. 8; pp. 1235-1258; Aug. 2002.
Luechinger et al.; Force and torque effects of a 1.5-tesla MRI scanner of cardiac pacemakers and ICDs; Journal of PACE; vol. 24; No. 2; pp. 199-205; Feb. 2001.
Luechinger et al.; In vivo heating of pacemaker leads during magnetic resonance imaging; European Heart Journal; vol. 26; pp. 376-383; Feb. 2005.
Lüchinger ; Safety aspects of cardiac pacemakers in magnetic resonance imaging; Dissertation submitted to the Swiss Federal Institute of Technology Zurich; 137 pages; 2002 (month unavailable).
Nyenhuis et al.; MRI and Implanted Medical Devices: Basic Interactions with an emphasis on heating; vol. 5; No. 3; pp. 467-480; Sep. 2005.
Shellock et al.; Cardiac pacemaker: In vitro assessment at 1.5 T; Am Heart J; vol. 151; No. 2; pp. 436-443; Feb. 2006.
Khairkhahan et al.; U.S. Appl. No. 13/272,074 entitled "Delivery catheter systems and methods," filed Oct. 12, 2011.
Khairkhahan et al.; U.S. Appl. No. 13/272,082 entitled "Leadless cardiac pacemaker with anti-unscrewing feature," filed Oct. 12, 2011.
Ostroff, Alan; U.S. Appl. No. 13/272,092 entitled "Temperature sensor for a leadless cardiac pacemaker," filed Oct. 12, 2011.
Khairkhahan et al.; U.S. Appl. No. 13/324,781 entitled "Delivery Catheter Systems and Methods," filed Dec. 13, 2011.
Jacobson et al.; U.S. Appl. No. 13/277,151 entitled "Leadless cardiac pacemaker with conducted communication," filed Oct. 19, 2011.
Khairkhahan et al.; U.S. Appl. No. 13/324,802 entitled "Pacemaker Retrieval Systems and Methods ," filed Dec. 13, 2011.
Khairkhahan et al.; U.S. Appl. No. 13/331,922 entitled "Leadless Pacemaker with Radial Fixation Mechanism ," filed Dec. 20, 2011.
PCT International Search Report dated Apr. 8, 2008.
Advisory Action mailed Aug. 19, 2014 for U.S. Appl. No. 13/277,151, filed Apr. 19, 2013, 5 pages.
Appeal Brief filed Jul. 13, 2012 for U.S. Appl. No. 12/953,282, filed Nov. 23, 2010, 17 pages.
Appeal Brief filed Mar. 7, 2013 for U.S. Appl. No. 11/549,581, filed Oct. 13, 2006, 25 pages.
Appeal Brief filed Oct. 10, 2011 for U.S. Appl. No. 11/549,591, filed Oct. 13, 2006, 20 pages.
Communication of a Notice of Opposition mailed Oct. 24, 2014 for European Application No. 06836350.6, 35 pages.
Design of Cardiac Pacemakers, edited by J.G. Webster, 1995, Chapter 11.
Examiner's Answer to Appeal Brief mailed Aug. 30, 2012 for U.S. Appl. No. 12/953,282, filed Nov. 23, 2010, 6 pages.
Examiner's Answer to Appeal Brief mailed Mar. 13, 2012 for U.S. Appl. No. 11/549,591, filed Oct. 13, 2006, 12 pages.
Extended European Search Report for Application No. European Application No. 06836350.6 dated Nov. 20, 2009.
Extended European Search Report for Application No. European Application No. 12159212.5 dated Jun. 4, 2012.
Extended European Search Report for Application No. European Application No. 12159213.3 dated Jun. 4, 2012.
Extended European Search Report for Application No. European Application No. 12159214.1 dated Jun. 4, 2012.
Extended European Search Report for Application No. European Application No. 12159218.2 dated Jun. 4, 2012.
Extended European Search Report for Application No. European Application No. 12159219.0 dated Jun. 6, 2012.
Extended European Search Report for Application No. European Application No. 12159220.8 dated Jun. 4, 2012.
Extended European Search Report for Application No. European Application No. 12159222.4 dated Jun. 4, 2012.
Extended European Search Report for Application No. European Application No. 12841426.5 dated Jun. 2, 2015.
Final Office Action mailed Apr. 27, 2011 for U.S. Appl. No. 11/549,591, filed Oct. 13, 2006, 11 pages.
Final Office Action mailed Aug. 30, 2010 for U.S. Appl. No. 11/549,599, filed Oct. 13, 2006, 10 pages.
Final Office Action mailed Aug. 31, 2010 for U.S. Appl. No. 11/549,596, filed Oct. 13, 2006, 10 pages.
Final Office Action mailed Feb. 23, 2012 for U.S. Appl. No. 12/953,282, filed Nov. 23, 2010, 12 pages.
Final Office Action mailed Jun. 24, 2014 for U.S. Appl. No. 13/277,151, filed Apr. 19, 2013, 22 pages.
Final Office Action mailed Nov. 25, 2009 for U.S. Appl. No. 11/549,599, filed Oct. 13, 2006, 14 pages.
Final Office Action mailed Nov. 27, 2009 for U.S. Appl. No. 11/549,596, filed Oct. 13, 2006, 10 pages.
Final Office Action mailed Oct. 16, 2012 for U.S. Appl. No. 11/549,581, filed Oct. 13, 2006, 28 pages.
International Preliminary Report on Patentability for Application No. PCT/US06/40564, dated Sep. 30, 2008, 26 pages.
International Preliminary Report on Patentability for Application No. PCT/US12/57776, dated Apr. 22, 2014, 8 pages.
International Search Report for Application No. PCT/US12/57776, mailed Jan. 10, 2013, 2 pages.
International Searching Authority, "Notification of Transmittal of the International Search Report and the Written Opinion of the International Searching Authority, or the Declaration," International Application No. PCT/US06/40564, Apr. 8, 2008, 29 pages.
International Searching Authority, "Notification of Transmittal of the International Search Report and the Written Opinion of the International Searching Authority, or the Declaration," International Application No. PCT/US12/57776, Jan. 10, 2013, 12 pages.
Jacobson P.M., et al., U.S. Appl. No. 12/953,282 entitled "Leadless Cardiac Pacemaker Triggered by Conductive Communication," filed Nov. 23, 2010.
Jacobson P.M., et al., U.S. Appl. No. 13/109,728 entitled "Programmer for Biostimulator System," filed May 17, 2011.
Jacobson P.M., et al., U.S. Appl. No. 13/191,229 entitled "Implantable Biostimulator Delivery System," filed Jul. 26, 2011.
Jacobson P.M., et al., U.S. Appl. No. 13/708,732 entitled "Leadless Cardiac Pacemaker Triggered by Conductive Communication," filed Dec. 7, 2012.
Jacobson P.M., et al., U.S. Appl. No. 13/866,803 entitled "Leadless Cardiac Pacemaker System for Usage in Combination with an Implantable Cardioverter-Defribrillator," filed Apr. 19, 2013.
Jacobson P.M., et al., U.S. Appl. No. 13/098,266 entitled "Rate Responsive Leadless Cardiac Pacemaker," filed Apr. 29, 2011.
Non-Final Office Action mailed Aug. 28, 2012 for U.S. Appl. No. 11/549,599, filed Oct. 13, 2006, 12 pages.
Non-Final Office Action mailed Dec. 1, 2011 for U.S. Appl. No. 13/109,728, filed May 17, 2011, 16 pages.
Non-Final Office Action mailed Dec. 9, 2008 for U.S. Appl. No. 11/649,591, filed Oct. 13 2006, 35 pages.
Non-Final Office Action mailed Dec. 9, 2008 for U.S. Appl. No. 11/549,599, filed Oct. 13, 2006, 35 pages.
Non-Final Office Action mailed Feb. 4, 2009 for U.S. Appl. No. 11/549,605, filed Oct. 13, 2006, 11 pages.
Non-Final Office Action mailed Jun. 13, 2013 for U.S. Appl. No. 13/866,803, filed Apr. 19, 2013, 11 pages.
Non-Final Office Action mailed Jun. 22, 2012 for U.S. Appl. No. 11/549,581, filed Oct. 13, 2006, 27 pages.

(56) References Cited

OTHER PUBLICATIONS

Non-Final Office Action mailed Jun. 7, 2011 for U.S. Appl. No. 12/953,282, filed Nov. 23, 2010, 12 pages.
Non-Final Office Action mailed Mar. 17, 2010 for U.S. Appl. No. 11/549,596, filed Oct. 13, 2006, 8 pages.
Non-Final Office Action mailed Mar. 17, 2010 for U.S. Appl. No. 11/549,599, filed Oct. 13, 2006, 9 pages.
Non-Final Office Action mailed May 11, 2010 for U.S. Appl. No. 11/549,605, filed Oct. 13, 2006, 16 pages.
Non-Final Office Action mailed May 12, 2010 for U.S. Appl. No. 11/549,591, filed Oct. 13, 2006, 11 pages.
Non-Final Office Action mailed May 21, 2012 for U.S. Appl. No. 11/549,596, filed Oct. 13, 2006, 8 pages.
Non-Final Office Action mailed May 4, 2012 for U.S. Appl. No. 11/549,599, filed Oct. 13, 2006, 42 pages.
Non-Final Office Action mailed Nov. 24, 2010 for U.S. Appl. No. 11/549,591, filed Oct. 13, 2006, 10 pages.
Non-Final Office Action mailed Nov. 25, 2008 for U.S. Appl. No. 11/549,596, filed Oct. 13, 2006, 29 pages.
Non-Final Office Action mailed Oct. 1, 2013 for U.S. Appl. No. 13/866,803, filed Apr. 19, 2013, 11 pages.
Non-Final Office Action mailed Sep. 11, 2013 for U.S. Appl. No. 13/277,151, filed Apr. 19, 2013, 18 pages.
Notice of Allowance mailed Feb. 22, 2011 for U.S. Appl. No. 11/549,605, filed Oct. 13, 2006, 4 pages.
Notice of Allowance mailed Jan. 23, 2013 for U.S. Appl. No. 11/549,599, filed Oct. 13, 2006, 7 pages.
Notice of Allowance mailed Jan. 5, 2011 for U.S. Appl. No. 11/549,605, filed Oct. 13, 2006, 4 pages.
Notice of Allowance mailed Jun. 25, 2012 for U.S. Appl. No. 13/109,728, filed May 17, 2011, 7 pages.
Notice of Allowance mailed Mar. 26, 2014 for U.S. Appl. No. 13/866,803, filed Apr. 19, 2013, 11 pages.
Notice of Allowance mailed Sep. 10, 2012 for U.S. Appl. No. 11/549,596, filed Oct. 13, 2006, 5 pages.
Notice of Allowance mailed Sep. 25, 2014 for U.S. Appl. No. 13/277,151, filed Apr. 19, 2013, 10 pages.
Ostroff A., et al., U.S. Appl. No. 12/568,513 entitled "MRI Compatible Leadless Cardiac Pacemaker," filed Sep. 28, 2009.
Ostroff A., et al., U.S. Appl. No. 12/698,969 entitled "Leadless Cardiac Pacemaker with Secondary Fixation Capability," filed Feb. 2, 2010.
Ostroff A., et al., U.S. Appl. No. 13/910,896 entitled "Leadless Pacemaker with Multiple Electrodes," filed Jun. 5, 2013.
Ostroff A., et al., U.S. Appl. No. 13/915,560 entitled "MRI Compatible Leadless Cardiac Pacemaker," filed Jun. 11, 2013.
Patent Board Decision on Appeal mailed Jun. 1, 2015 for U.S. Appl. No. 11/549,591, filed Oct. 13, 2006, 10 pages.
Pertijs M., et al., U.S. Appl. No. 13/901,414 entitled "Temperature Sensor for a Leadless Cardiac Pacemaker," filed May 23, 2013.
Reply Brief filed May 8, 2012 for U.S. Appl. No. 11/549,591, filed Oct. 13, 2006, 4 pages.
Reply Brief filed Oct. 29, 2012 for U.S. Appl. No. 12/953,282, filed Nov. 23, 2010, 4 pages.
Response mailed Dec. 22, 2011 to Non-Final Office Action for U.S. Appl. No. 12/953,282, filed Nov. 23, 2010, 9 pages.
Terminal Disclaimer filed Sep. 12, 2014 for U.S. Appl. No. 13/277,151, filed Apr. 19, 2013, 2 pages.
Varady E., et al., U.S. Appl. No. 13/669,242 entitled "Leadless Cardiac Pacemaker with Integral Battery and Redundant Welds," filed Nov. 5, 2012.
Written Opinion for Application No. PCT/US06/40564, mailed Apr. 8, 2008, 25 pages.
Written Opinion for Application No. PCT/US12/57776, mailed Jan. 10, 2013, 7 pages.
Pacesetter Request for Adverse Judgment filed Sep. 10, 2015, Interference No. 106,031, 3 pages.
Order—Miscellaneous, Entered Sep. 9, 2015, Interference No. 106,031, 4 pages.
Judgment, Entered Sep. 15, 2015, Interference No. 106,031, 3 pages.
Notice of Allowance mailed Oct. 7, 2015 for U.S. Appl. No. 11/549,591, filed Oct. 13, 2006, 7 pages.
Notice of Allowance mailed Aug. 21, 2015 for U.S. Appl. No. 11/549,591, filed Oct. 13, 2006, 7 pages.
Patent Board Decision on Appeal mailed May 27, 2015 for U.S. Appl. No. 12/953,282, filed Nov. 23, 2010, 11 pages.
Notice of Allowance mailed Nov. 23, 2015 for U.S. Appl. No. 12/953,282, filed Nov. 23, 2010, 6 pages.
Notice of Allowance mailed May 22, 2015 for U.S. Appl. No. 13/098,266, filed Apr. 29, 2011, 5 pages.
Advisory Action mailed Apr. 20, 2015 for U.S. Appl. No. 13/098,266, filed Apr. 29, 2011, 5 pages.
Final Action mailed Jan. 29, 2015 for U.S. Appl. No. 13/098,266, filed Apr. 29, 2011, 17 pages.
Non-Final Action mailed Aug. 22, 2014 for U.S. Appl. No. 13/098,266, filed Apr. 29, 2011, 24 pages.
Advisory Action mailed May 5, 2014 for U.S. Appl. No. 13/098,266, filed Apr. 29, 2011, 6 pages.
Final Action mailed Feb. 27, 2014 for U.S. Appl. No. 13/098,266, filed Apr. 29, 2011, 20 pages.
Non-Final Action mailed Oct. 10, 2013 for U.S. Appl. No. 13/098,266, filed Apr. 29, 2011, 15 pages.
Non-Final Action mailed May 31, 2013 for U.S. Appl. No. 13/098,266, filed Apr. 29, 2011, 15 pages.
Advisory Action mailed Aug. 31, 2012 for U.S. Appl. No. 13/098,266, filed Apr. 29, 2011, 3 pages.
Final Action mailed Jun. 22, 2012 for U.S. Appl. No. 13/098,266, filed Apr. 29, 2011, 13 pages.
Non-Final Action mailed Nov. 25, 2011 for U.S. Appl. No. 13/098,266, filed Apr. 29, 2011, 15 pages.
Notice of Allowance mailed Jul. 8, 2014 for U.S. Appl. No. 13/191,229, filed Jul. 26, 2011, 7 pages.
Final Office Action mailed Apr. 18, 2014 for U.S. Appl. No. 13/191,229, filed Jul. 26, 2011, 14 pages.
Non-Final Office Action mailed Sep. 11, 2013 for U.S. Appl. No. 13/191,229, filed Jul. 26, 2011, 9 pages.
Final Office Action mailed May 22, 2013 for U.S. Appl. No. 13/191,229, filed Jul. 26, 2011, 8 pages.
Non-Final Office Action mailed Jan. 30, 2013 for U.S. Appl. No. 13/191,229, filed Jul. 26, 2011, 7 pages.
Appeal Brief filed Nov. 20, 2012 for U.S. Appl. No. 13/191,229, filed Jul. 26, 2011, 9 pages.
Advisory Action mailed Sep. 25, 2012 for U.S. Appl. No. 13/191,229, filed Jul. 26, 2011, 3 pages.
Final Office Action mailed Jun. 28, 2012 for U.S. Appl. No. 13/191,229, filed Jul. 26, 2011, 7 pages.
Non-Final Office Action mailed Dec. 8, 2011 for U.S. Appl. No. 13/191,229, filed Jul. 26, 2011, 6 pages.
Notice of Allowance mailed May 12, 2014 for U.S. Appl. No. 13/708,732, filed Dec. 7, 2012, 7 pages.
Final Office Action mailed Jan. 2, 2014 for U.S. Appl. No. 13/708,732, filed Dec. 7, 2012, 8 pages.
Non-Final Office Action mailed Jun. 12, 2013 for U.S. Appl. No. 13/708,732, filed Dec. 7, 2012, 6 pages.
Non-Final Office Action mailed Feb. 22, 2013 for U.S. Appl. No. 13/708,732, filed Dec. 7, 2012, 6 pages.
Notice of Allowance mailed Jun. 4, 2014 for U.S. Appl. No. 13/654,240, filed Oct. 17, 2012, 9 pages.
Non-Final Office Action mailed Jan. 23, 2014 for U.S. Appl. No. 13/654,240, filed Oct. 17, 2012, 9 pages.
Advisory Action mailed Dec. 6, 2013 for U.S. Appl. No. 13/654,240, filed Oct. 17, 2012, 5 pages.
Final Office Action mailed Sep. 30, 2013 for U.S. Appl. No. 13/654,240, filed Oct. 17, 2012, 11 pages.
Non-Final Office Action mailed May 13, 2013 for U.S. Appl. No. 13/654,240, filed Oct. 17, 2012, 7 pages.
Notice of Allowance mailed Sep. 23, 2015 for U.S. Appl. No. 14/318,201, filed Jun. 27, 2014, 8 pages.
Terminal Disclaimer filed Sep. 16, 2015 for U.S. Appl. No. 14/318,201, filed Jun. 27, 2014, 2 pages.
Non-Final Office Action mailed Apr. 30, 2015 for U.S. Appl. No. 14/318,201, filed Jun. 27, 2014, 7 pages.

(56) References Cited

OTHER PUBLICATIONS

Non-Final Office Action mailed Dec. 2, 2014 for U.S. Appl. No. 14/318,201, filed Jun. 27, 2014, 10 pages.
Notice of Allowance mailed Aug. 20, 2015 for U.S. Appl. No. 13/277,151, filed Apr. 19, 2013, 8 pages.
Non-Final Office Action mailed Feb. 5, 2015 for U.S. Appl. No. 13/277,151, filed Apr. 19, 2013, 19 pages.
Non-Final Office Action mailed Sep. 16, 2013 for U.S. Appl. No. 13/708,732, filed Dec. 7, 2012, 6 pages.
Applicant Initiated Interview Summary mailed Sep. 17, 2014 for U.S. Appl. No. 13/277,151, filed Apr. 4, 2013, 3 pages.
Non-Final Office Action mailed Nov. 18, 2015 for U.S. Appl. No. 14/885,853, filed Oct. 16, 2015, 6 pages.
Notice of Allowance mailed Apr. 29, 2011 for U.S. Appl. No. 11/549,574, filed Oct. 13, 2006, 13 pages.
Final Office Action mailed Dec. 22, 2010 for U.S. Appl. No. 11/549,574, filed Oct. 13, 2006, 14 pages.
Non-Final Office Action mailed Jul. 8, 2010 for U.S. Appl. No. 11/549,574, filed Oct. 13, 2006, 13 pages.
Final Office Action mailed Oct. 21, 2009 for U.S. Appl. No. 11/549,574, filed Oct. 13, 2006, 13 pages.
Non-Final Office Action mailed May 13, 2009 for U.S. Appl. No. 11/549,574, filed Oct. 13, 2006, 13 pages.
Non-Final Office Action mailed Oct. 1, 2009 for U.S. Appl. No. 11/549,591, filed Oct. 13, 2006, 10 pages.
Applicant Summary of Interview with Examiner, mailed Aug. 22, 2012 for U.S. Appl. No. 11/549,596, filed Oct. 13, 2006, 1 page.
Electronic Terminal Disclaimer filed Nov. 21, 2012 for U.S. Appl. No. 11/549,599, filed Oct. 13, 2006, 2 pages.
Notice of Allowance mailed Dec. 27, 2010 for U.S. Appl. No. 11/549,603, filed Oct. 13, 2006, 6 pages.
Examiner Interview Summary Record mailed Oct. 13, 2010 for U.S. Appl. No. 11/549,603, filed Oct. 13, 2006, 4 pages.
Non-Final Office Action mailed Aug. 31, 2010 for U.S. Appl. No. 11/549,603, filed Oct. 13, 2006, 14 pages.
Final Office Action mailed Jan. 21, 2010 for U.S. Appl. No. 11/549,603, filed Oct. 13, 2006, 17 pages.
Non-Final Office Action mailed May 22, 2009 for U.S. Appl. No. 11/549,603, filed Oct. 13, 2006, 17 pages.
Examiner Interview Summary Record mailed Oct. 13, 2010 for U.S. Appl. No. 11/549,605, filed Oct. 13, 2006, 4 pages.
Final Office Action mailed Jul. 7, 2009 for U.S. Appl. No. 11/549,605, filed Oct. 13, 2006, 15 pages.

* cited by examiner

LEADLESS CARDIAC PACEMAKER

CROSS REFERENCE TO RELATED APPLICATIONS

This application claims the benefit of priority to and incorporates herein by reference in its entirety for all purposes, Provisional U.S. Patent Application Nos.: 60/726,706 entitled "LEADLESS CARDIAC PACEMAKER WITH CONDUCTED COMMUNICATION," filed Oct. 14, 2005; 60/761,531 entitled "LEADLESS CARDIAC PACEMAKER DELIVERY SYSTEM," filed Jan. 24, 2006; 60/729,671 entitled "LEADLESS CARDIAC PACEMAKER TRIGGERED BY CONDUCTED COMMUNICATION," filed Oct. 24, 2005; 60/737,296 entitled "SYSTEM OF LEADLESS CARDIAC PACEMAKERS WITH CONDUCTED COMMUNICATION," filed Nov. 16, 2005; 60/739,901 entitled "LEADLESS CARDIAC PACEMAKERS WITH CONDUCTED COMMUNICATION FOR USE WITH AN IMPLANTABLE CARDIOVERTER-DEFIBRILLATOR," filed Nov. 26, 2005; 60/749,017 entitled "LEADLESS CARDIAC PACEMAKER WITH CONDUCTED COMMUNICATION AND RATE RESPONSIVE PACING," filed Dec. 10, 2005; and 60/761,740 entitled "PROGRAMMER FOR A SYSTEM OF LEADLESS CARDIAC PACEMAKERS WITH CONDUCTED COMMUNICATION," filed Jan. 24, 2006; all by Peter M. Jacobson.

BACKGROUND

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Cardiac pacing is usually performed by a pulse generator implanted subcutaneously or sub-muscularly in or near a patient's pectoral region. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Pulse generator parameters are usually interrogated and modified by a programming device outside the body, via a loosely-coupled transformer with one inductance within the body and another outside, or via electromagnetic radiation with one antenna within the body and another outside.

Although more than one hundred thousand conventional cardiac pacing systems are implanted annually, several well-known difficulties exist.

For example, a pulse generator, when located subcutaneously, presents a bulge in the skin that patients can find unsightly or unpleasant. Patients can manipulate or "twiddle" the device. Even without persistent twiddling, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The at least one male connector mates with at least one corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. The complex connection between connectors and leads provides multiple opportunities for malfunction.

For example, failure to introduce the lead pin completely into the terminal block can prevent proper connection between the generator and electrode.

Failure to insert a screwdriver correctly through the setscrew slot, causing damage to the slot and subsequent insulation failure.

Failure to engage the screwdriver correctly in the setscrew can cause damage to the setscrew and preventing proper connection.

Failure to tighten the setscrew adequately also can prevent proper connection between the generator and electrode, however over-tightening of the setscrew can cause damage to the setscrew, terminal block, or lead pin, and prevent disconnection if necessary for maintenance.

Fluid leakage between the lead and generator connector moldings, or at the setscrew cover, can prevent proper electrical isolation.

Insulation or conductor breakage at a mechanical stress concentration point where the lead leaves the generator can also cause failure.

Inadvertent mechanical damage to the attachment of the connector molding to the generator can result in leakage or even detachment of the molding.

Inadvertent mechanical damage to the attachment of the connector molding to the lead body, or of the terminal pin to the lead conductor, can result in leakage, an open-circuit condition, or even detachment of the terminal pin and/or molding.

The lead body can be cut inadvertently during surgery by a tool, or cut after surgery by repeated stress on a ligature used to hold the lead body in position. Repeated movement for hundreds of millions of cardiac cycles can cause lead conductor breakage or insulation damage anywhere along the lead body.

Although leads are available commercially in various lengths, in some conditions excess lead length in a patient exists and is to be managed. Usually the excess lead is coiled near the pulse generator. Repeated abrasion between the lead body and the generator due to lead coiling can result in insulation damage to the lead.

Friction of the lead against the clavicle and the first rib, known as subclavian crush, can result in damage to the lead.

In many applications, for example dual-chamber pacing, multiple leads are implanted in the same patient and sometimes in the same vessel. Abrasion between the leads for hundreds of millions of cardiac cycles can cause insulation breakdown or even conductor failure.

Communication between the implanted pulse generator and external programmer in a conventional pacing system uses a telemetry coil or antenna and associated circuitry in the pulse generator with inherent complexity that increases the size and cost of both the implantable and external devices. Moreover, the power budget from the pulse generator battery for communication typically exceeds power used for pacing by one or more orders of magnitude, introducing a requirement for battery power capability that can prevent selection of the most optimal battery construction for the otherwise low-power requirements of pacing.

SUMMARY

According to an embodiment of a cardiac pacing system, a leadless cardiac pacemaker is configured for implantation in electrical contact with a cardiac chamber and configured for leadless pacing.

BRIEF DESCRIPTION OF THE DRAWINGS

Embodiments of the invention relating to both structure and method of operation may best be understood by referring to the following description and accompanying drawings, in which similar reference characters denote similar elements throughout the several views.

DETAILED DESCRIPTION

Figure 1A:
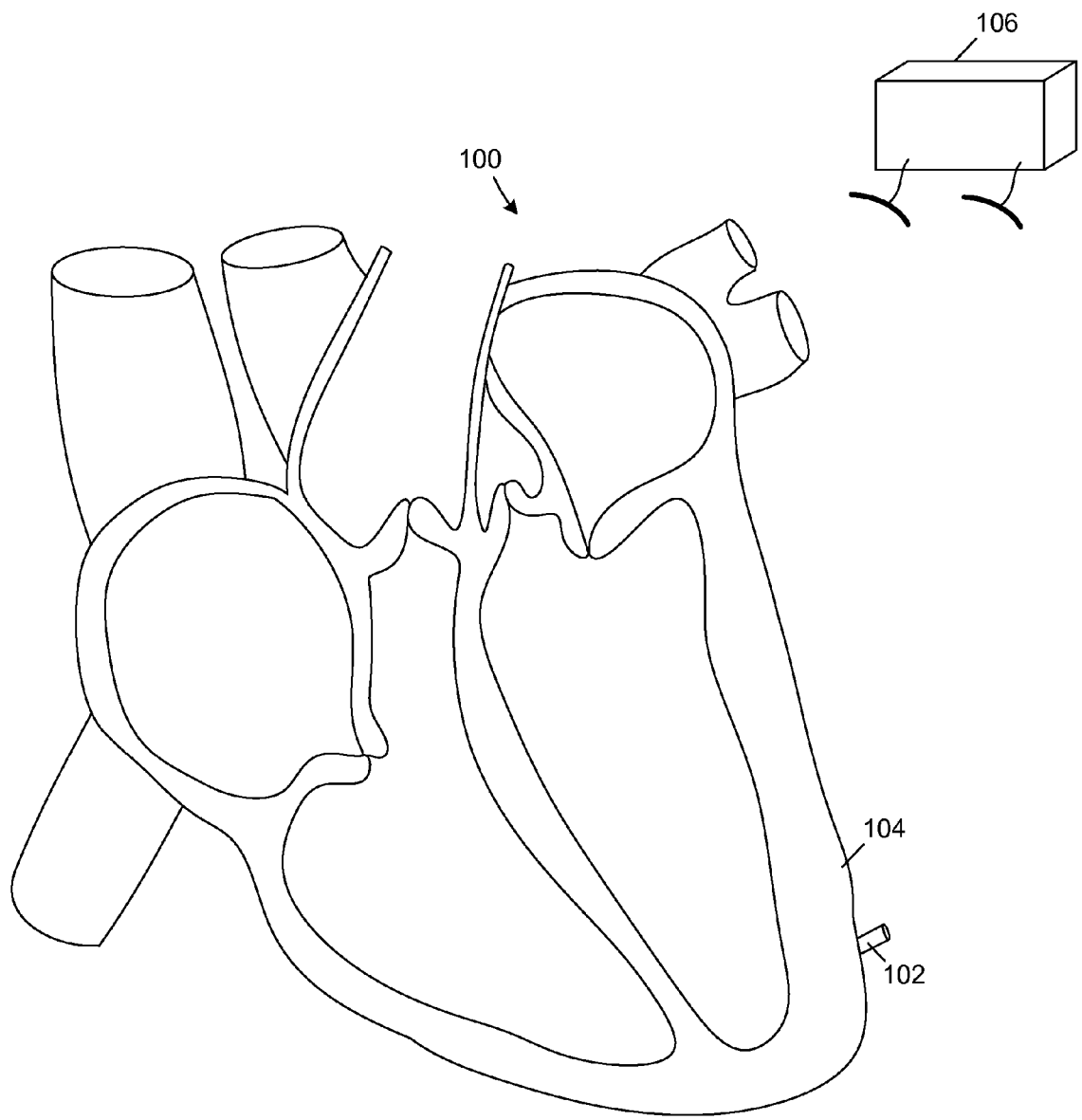
FIG. 1A is a pictorial diagram showing an embodiment of a leadless cardiac pacemaker.

A leadless biostimulator is adapted for conducted communication.

In some embodiments of a leadless biostimulator, a leadless cardiac pacemaker can communicate by conducted communication, representing a substantial departure from the conventional pacing systems. For example, an illustrative cardiac pacing system can perform cardiac pacing that has many of the advantages of conventional cardiac pacemakers while extending performance, functionality, and operating characteristics with one or more of several improvements.

In a particular embodiment of a cardiac pacing system, cardiac pacing is provided without a pulse generator located in the pectoral region or abdomen, without an electrode-lead separate from the pulse generator, without a communication coil or antenna, and without an additional requirement on battery power for transmitted communication.

An embodiment of a cardiac pacing system configured to attain these characteristics comprises a leadless cardiac pacemaker that is substantially enclosed in a hermetic housing suitable for placement on or attachment to the inside or outside of a cardiac chamber. The pacemaker has at least two electrodes located within, on, or near the housing, for delivering pacing pulses to muscle of the cardiac chamber and optionally for sensing electrical activity from the muscle, and for bidirectional communication with at least one other device within or outside the body. The housing contains a primary battery to provide power for pacing, sensing, and communication, for example bidirectional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In accordance with some embodiments, a cardiac pacemaker is adapted for implantation in the human body. In a particular embodiment, a leadless cardiac pacemaker can be adapted for implantation adjacent to the inside or outside wall of a cardiac chamber, using two or more electrodes located within, on, or within two centimeters of the housing of the pacemaker, for pacing the cardiac chamber upon receiving a triggering signal from at least one other device within the body.

For example, some embodiments of a leadless pacemaker can be configured for implantation adjacent to the inside or outside wall of a cardiac chamber without the need for a connection between the pulse generator and an electrode-lead, and without the need for a lead body.

Other example embodiments provide communication between the implanted leadless pulse generator and a device internal or external to the body, using conducted communication via the same electrodes used for pacing, without the need for an antenna or telemetry coil.

Some example embodiments can provide communication between the implanted leadless pacemaker pulse generator and a device internal or external to the body, with power requirements similar to those for cardiac pacing, to enable optimization of battery performance. In an illustrative embodiment, outgoing telemetry can be adapted to use no additional energy other than the energy contained in the pacing pulse. The telemetry function can be supplied via conducted communication using pacing and sensing electrodes as the operative structures for transmission and reception.

Figure 1B:
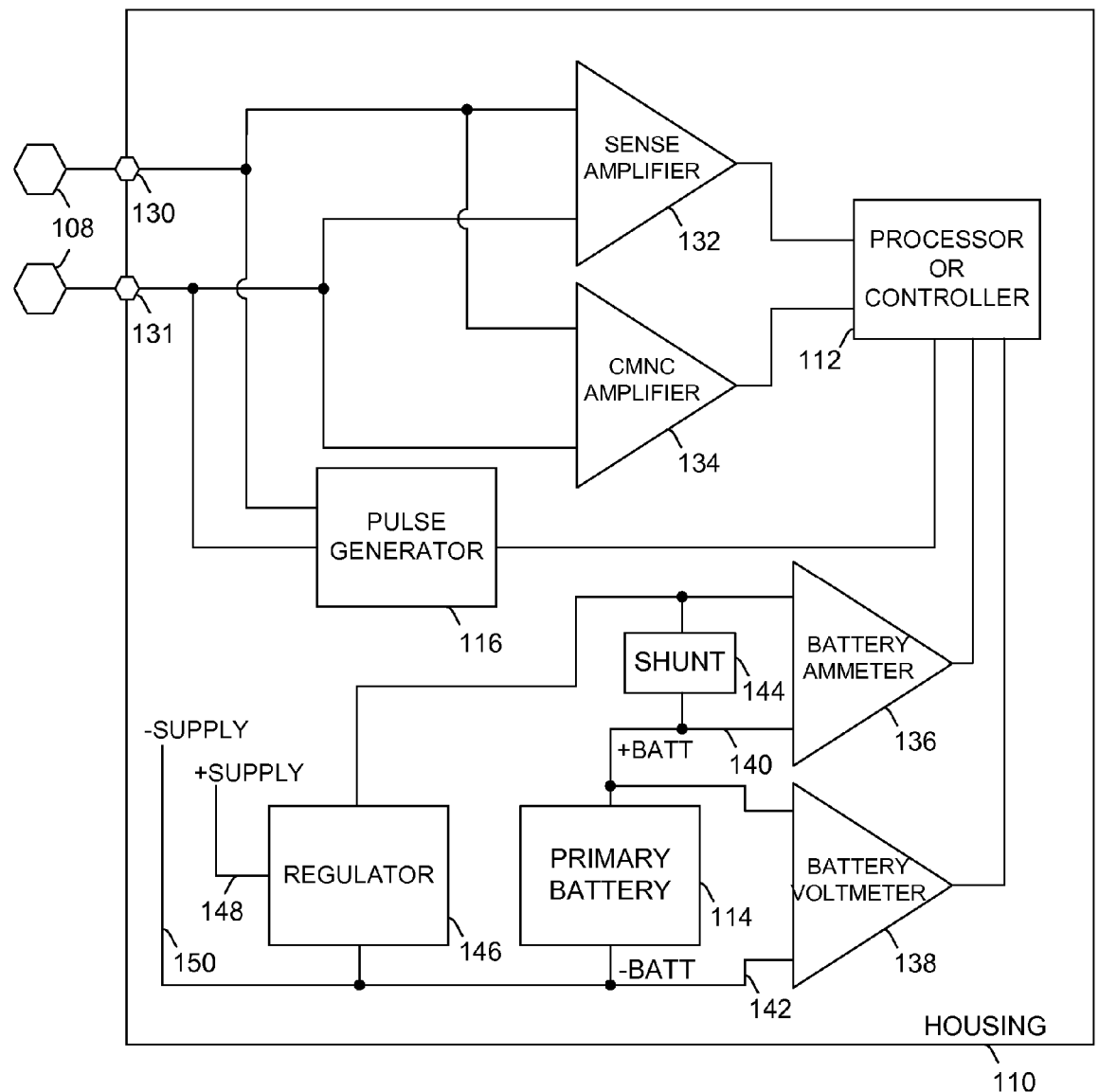
FIG. 1B is a schematic block diagram showing interconnection of operating elements of an embodiment of the illustrative leadless cardiac pacemaker.

Referring to FIGS. 1A and 1B, a pictorial view that is not shown to scale and a schematic block diagram respectively depict an embodiment of a leadless biostimulator 102, for example cardiac pacemaker 102, that generates pacing pulses and derives operating power from an internal source. The leadless cardiac pacemaker 102 comprises a housing 110, two or more electrodes 108 coupled to the housing 110, and a pulse generator 116 hermetically contained within the housing 110 and electrically coupled to the electrodes 108. The pulse generator 116 generates and delivers electrical pulses via the electrodes 108. A processor 112 is hermetically contained within the housing 110 and is communicatively coupled to the pulse generator 116 and the electrodes 108. The processor 112 controls electrical pulse delivery according to programmed instructions. A power supply is hermetically contained within the housing 110 and coupled to the pulse generator 116. The power supply supplies all energy for operations and electrical pulse generation as a source internal to the housing 110. In the illustrative embodiment, the power supply includes a primary battery with an energy density of at least 3 watt-hours/cubic centimeter (W·h/cc).

In various embodiments, the electrodes 108 can be formed integrally to the housing 110 or may be coupled but separated by a distance, for example up to 2 cm, from the housing 110 as is typical for a screw-in electrode.

The processor 112 communicates with a device external to the pacemaker, for example typically an external programmer or another implanted device 106, by conducted communication signals transmitted via the electrodes 108. Communication is typically bidirectional although some implementations may include only one-way communication, either to or from the pacemaker 102. The processor 112 controls electrical pulse delivery based on one or more programmable parameters and can be programmed by conducted communication signals transmitted over the electrodes 108.

The pulse generator 116 can selectively generate and deliver electrical energy in a stimulation pulse to two or more of the electrodes 108 to cause a contraction of a patient's heart in response to control signals from the processor 112. In some implementations, the pulse generator 116 can generate and deliver electrical energy with the stimulation pulse interrupted by one or more notches that convey information to a device 106 external to the pacemaker 102. The processor 112 can encode the information to be conveyed on a pacing pulse. For example, the processor 112 can communicate control signals to the pulse generator 116 specifying characteristics of the notch or notches which define the conveyed information.

In a typical embodiment, the pulse generator 116 can generate and deliver electrical energy with the stimulation pulse interrupted by one or more notches that convey information to a device 106 external to the pacemaker 102. For example, the conveyed information can be programmable parameter settings, event counts, power-supply voltage, power-supply current, and other data. The notches can be any suitable width. One example of a suitable notch width is approximately 15 microseconds.

In some embodiments, the pulse generator 116 generates and delivers the stimulation pulse interrupted by a notch or notches that are timed to occur within selected timing windows. The selected timing windows can be separated by any suitable spacing. One example of a suitable spacing between timing windows is approximately 100 microseconds.

In other embodiments or in some conditions, the pulse generator 116 can be configured for generating and delivering electrical energy in a series of stimulation pulses with time between the stimulation pulses selectively varied to convey information to a device 106 external to the pacemaker 102. The variation of time between pulses can be controlled to any suitable variation. One example of a suitable allowable variation is less than a total of approximately 10 milliseconds.

The illustrative power supply can be a primary battery 114 such as a beta-voltaic converter that obtains electrical energy from radioactivity. In some embodiments, the power supply can be selected as a primary battery 114 that has a volume less than approximately 1 cubic centimeter.

In an illustrative embodiment, the primary battery 114 can be selected to source no more than 70 microwatts instantaneously since a higher consumption may cause the voltage across the battery terminals to collapse. Accordingly in one illustrative embodiment the circuits depicted in FIG. 1B can be designed to consume no more than a total of 64 microwatts. The design avoids usage of a large filtering capacitor for the power supply or other accumulators such as a supercapacitor or rechargeable secondary cell to supply peak power exceeding the maximum instantaneous power capability of the battery, components that would add volume and cost.

In various embodiments, the system can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

Implantable systems that communicate via long distance radio-frequency (RF) schemes, for example Medical Implant Communication Service (MICS) transceivers, which exhibit a peak power requirement on the order of 10 milliwatts, and other RF or inductive telemetry schemes are unable to operate without use of an additional accumulator. Moreover, even with the added accumulator, sustained operation would ultimately cause the voltage across the battery to collapse.

In some pacemaker implementations, a battery ammeter 136 can be coupled between the primary battery 114 and the processor 112 for indicating battery current drain and indirectly indicating device health for usage by the processor 112. Some implementations can have a battery voltmeter 138 coupled between the primary battery 114 and the processor 112 for indicating battery voltage for usage by the processor 112.

In some implementations, the leadless cardiac pacemaker 102 can also comprise a regulator circuit 146 which is electrically connected between the power supply and pacemaker circuitry. The regulator circuit 146 regulates the voltage supply for powering pacemaker circuitry.

Figure 2:
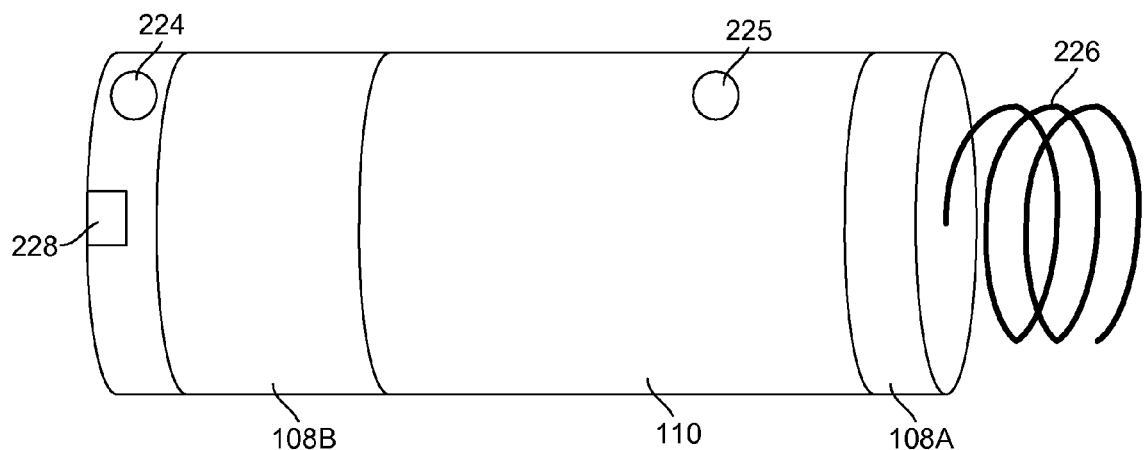
FIG. 2 is a pictorial diagram showing the physical location of some elements of an embodiment of a leadless biostimulator.
Figure 3:
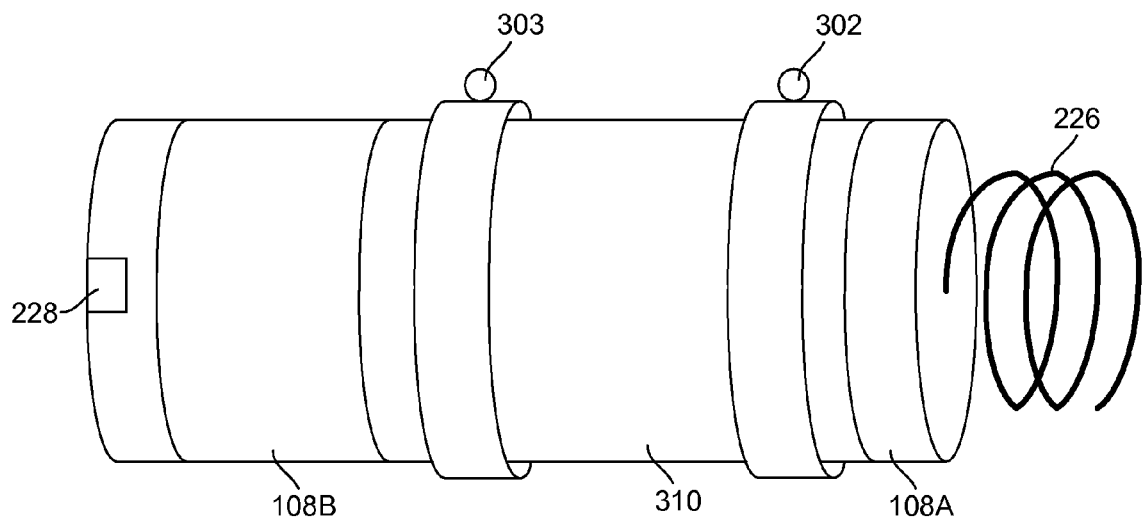
FIG. 3 is a pictorial diagram that depicts the physical location of some elements in an alternative embodiment of a leadless biostimulator.

Referring to FIGS. 2 and 3, pictorial diagrams show embodiments of leadless cardiac pacemakers 102. In the illustrative embodiments, the pacemaker 102 has a cylindrical housing 110, 310 and the electrodes comprise annular electrodes 108A, 108B and located at extremities of the housing.

As shown in FIG. 2, the housing 110 is constructed from a ceramic material and the electrodes 108A, 108B can be deposited on the ceramic material.

In contrast, FIG. 3 depicts a pacemaker 102 comprising a housing 310 constructed from titanium or stainless steel and coated over part of an exterior surface with a silicone rubber, polyurethane insulating material, or other biocompatible insulating material. The housing 310 constructed from titanium or stainless steel can function as one of the electrodes.

The leadless cardiac pacemaker 102 can further comprise a tissue connector 224, 225, 226, 302, 303 adapted to affix the housing 110, 310 to cardiac muscle 104. In various embodiments, the tissue connector can be a helix 226 configured to rotatingly advance into the cardiac muscle 104, one or more members pierced with a hole 224, 225 for passing a suture, one or more tines, and other structures.

Referring again to FIG. 1B, another embodiment of a leadless cardiac pacemaker 102 comprises a housing 110, two or more electrodes 108 formed integrally to the housing 110 or at a distance of up to 2 centimeters from the housing 100, and a pulse generator 116 hermetically contained within the housing 110 and electrically coupled to the electrodes 108. The pulse generator 116 generates and delivers electrical pulses to the electrodes 108. The pacemaker 102 further comprises one or more amplifiers 132, 134 hermetically contained within the housing 110 and electrically coupled to the electrodes 108. The amplifiers 132, 134 amplify signals received from the electrodes 108. A processor 112 is hermetically contained within the housing 110 and communicatively coupled to the pulse generator 116, the amplifiers 132, 134, and the electrodes 108. The processor 112 receives amplifier output signals from the amplifiers 132, 134 and controls electrical pulse delivery according to programmed instructions. A power supply is hermetically contained within the housing 110 and coupled to the pulse generator 116. The power supply supplies energy for operations and electrical pulse generation as a source internal to the housing 110.

An amplifier can be a cardiac sensing amplifier 132 that detects signals associated with a cardiac contraction from at least two of the electrodes 108 and sends a contraction output signal to the processor 112 in response to the cardiac contraction.

Another amplifier can be a communication amplifier 134 that detects an incoming communication signal from at least one device 106 external to the pacemaker from two or more of the electrodes 108 and sends a communication output signal to the processor 112 in response to the communication signal conveying information from the external device 106. The conveyed information can be programmable parameter settings. The communication amplifier 134 amplifies signals in any suitable frequency range. For example, the communication amplifier 134 can be configured to amplify signals in a frequency range from approximately 10 kHz to 100 kHz.

In a particular cardiac pacing system 100 embodiment, a leadless cardiac pacemaker 102 is configured for implantation in electrical contact with a cardiac chamber 104 and configured for leadless pacing, and powered by a battery 114 contained within a volume of less than one cubic centimeter.

In accordance with another embodiment of a leadless cardiac pacemaker 102, the pacemaker 102 comprises a housing 110, multiple electrodes 108 formed integrally to the housing 110 or coupled at a short distance of up to about 2 centimeters for example for usage of a screw-in electrode, and a pulse generator 116 hermetically contained within the housing 110 and electrically coupled to the electrodes 108. The pulse generator 116 generates and delivers electrical pulses to the electrodes 108 and causes cardiac contractions. The pulse generator 116 also conveys information to at least one device 106 external to the pacemaker 102 by conductive communication via the electrodes 108. The pacemaker 102 further comprises a plurality of amplifiers 132, 134 hermetically contained within the housing 110 and electrically coupled to the electrodes 108. The amplifier 132 amplifies signals received from the electrodes 108 for detecting cardiac contractions. The amplifier 134 receives information from the external device 106. A processor 112 is hermetically contained within the housing 110 and communicatively coupled to the pulse generator 116, the amplifiers 132, 134, and the electrodes 108. The processor 112 receives amplifier output signals from the amplifiers 132, 134, controls communications, and controls electrical pulse delivery according to programmed instructions. A power supply is hermetically contained within the housing 110 and coupled to the pulse generator 116. The power supply supplies energy for operations, communication, and electrical pulse generation as a source internal to the housing 110.

The pulse generator 116 is configured to consume a suitable electrical power. For example, the pacemaker 102 can be constructed so that the pulse generator 116 and rate limiter (not shown) consume a power of approximately 25 microwatts or less averaged over one cardiac cycle. The illustrative power consumption can be attained by limiting the recharging current of a pacing tank capacitor, for example.

The amplifiers 132, 134 can be configured to consume a suitable electrical power. For example, the pacemaker 102 can be constructed so that the amplifiers 132, 134 consume an electrical power of 30 microwatts or less.

The power supply is configured to consume and supply a suitable electrical power. For example, the power supply can be configured to consume a maximum electrical power of no more than 2 microwatts and configured to supply a minimum electrical power of approximately 64 microwatts.

The processor 112 can be configured to consume a suitable electrical power. For example, the pacemaker 102 can be constructed so that the processor 112 consumes a maximum electrical power of no more than 5 microwatts averaged over one cardiac cycle.

Referring again to FIG. 1B, another embodiment of a leadless cardiac pacemaker 102 comprises a housing 110, a plurality of electrodes 108 formed integrally to the housing 110 or coupled at a distance of up to two centimeters, and a pulse generator 116 hermetically contained within the housing 110 and electrically coupled to the electrodes 108. The pulse generator 116 generates and delivers electrical pulses to the electrodes 108 powered from a source contained entirely within the housing 110. The pacemaker 102 further comprises a logic 112 hermetically contained within the housing 110 and communicatively coupled to the pulse generator 116 and the electrodes 108. The logic 112 controls electrical pulse delivery according by logic execution of program instructions. A battery 114 powers the pacemaker 102 and has a volume of less than one cubic centimeter and a minimum lifetime of five years.

In accordance with another embodiment of a cardiac pacing system 100, a leadless cardiac pacemaker 102 comprises a housing 110, a plurality of electrodes 108 formed integrally to the housing 110 or coupled at a short distance, and a pulse generator 116 hermetically contained within the housing 110 and electrically coupled to the electrodes 108. The pulse generator 116 generates and delivers electrical pulses to the electrodes 108. A processor 112 is hermetically contained within the housing 110 and communicatively coupled to the pulse generator 116 and the electrodes 108. The processor 112 can control electrical pulse delivery and can communicate with one or more devices 106 external to the pacemaker 102 by conductive communication via the electrodes 108.

The processor 112 can be configured to control electrical pulse delivery according to one or more programmable parameters. The processor 112 is programmable by conducted communication signals transmitted via the electrodes 108.

The processor 112 communicates via bidirectional communication with one or more devices 106 external to the pacemaker 102 by conducted communication signals transmitted via the electrodes 108.

Again referring to FIG. 1B, the pacemaker 102 has functional elements substantially enclosed in a hermetic housing 110. The pacemaker has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to provide power for pacing, sensing, and communication. The housing 110 contains circuits 132 for sensing cardiac activity from the electrodes 108; circuits 134 for receiving information from at least one other device via the electrodes 108; and a pulse generator 116 for generating pacing pulses for delivery via the electrodes 108 and also for transmitting information to at least one other device via the electrodes 108. The pacemaker 102 further contains circuits for monitoring device health, for example a battery current monitor 136 and a battery voltage monitor 138. The pacemaker 102 further contains processor or controller circuits 112 for controlling these operations in a predetermined manner.

Information communicated on the incoming communication channel can include, but is not limited to, pacing rate, pulse duration, sensing threshold, and other parameters commonly programmed via external intervention as in conventional pacemakers. The information communicated on the outgoing communication channel can include, but is not limited to, programmable parameter settings, event counts such as pacing and sensing counts, battery voltage, battery current, and other information commonly displayed by external programmers used with conventional pacemakers. The outgoing communication channel can also echo information from the incoming channel to confirm correct programming.

Also shown in FIG. 1B, the primary battery 114 has positive terminal 140 and negative terminal 142. A suitable primary battery has an energy density of at least 3 W·h/cc, a power output of at least 70 microwatts, a volume less than 1 cubic centimeter, and a lifetime greater than 5 years.

One suitable primary battery uses beta-voltaic technology, licensed to BetaBatt Inc. of Houston, Tex., USA, and developed under a trade name DEC™ Cell, in which a silicon wafer captures electrons emitted by a radioactive gas such as tritium. The wafer is etched in a three-dimensional surface to capture more electrons. The battery is sealed in a hermetic package which entirely contains the low-energy particles emitted by tritium, rendering the battery safe for long-term human implant from a radiological-health standpoint. Tritium has a half-life of 12.3 years so that the technology is more than adequate to meet a design goal of a lifetime exceeding 5 years.

Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health.

The illustrative example avoids usage of radiofrequency (RF) communication to send pacing instructions to remote electrodes on a beat-to-beat basis to cause the remote electrodes to emit a pacing pulse. RF communication involves use of an antenna and modulation/demodulation unit in the remote electrode, which increase implant size significantly. Also, communication of pacing instructions on a beat-to-beat basis increases power requirements for the main body and the remote electrode. In contrast, the illustrative system and stimulator do not require beat-to-beat communication with any controlling main body.

The illustrative leadless pacemaker 102 includes an internal power source that can supply all energy for operations and pulse generation. In contrast, some conventional implanted pulse generators have remote pacing electrodes that receive some or all energy from an energy source through an RF induction technique, an energy transfer scheme that employs a large loop antenna on the remote electrode which increases size significantly. In addition, energy transfer with the RF induction technique is inefficient and is associated with a significant increase in battery size of the energy source. In contrast, the illustrative leadless pacemaker 102 uses an internal battery and does not require energy to be drawn from outside sources. Also in the conventional system, the energy source receives sensing information by RF communication from the remote electrodes and sends pacing instructions to the electrodes on a beat-to-beat basis in a configuration that uses an addressing scheme in which the identity of specific remote pacing electrodes is stored in the energy source memory. The conventional method can also be inefficient due to overhead for transmitting an identification number from/to a generic pacing electrode at implant and/or during sensing. The illustrative leadless pacemaker 102 avoids such overhead through a structure in which pulse generation functionality is independent within a single implantable body.

Another conventional technology uses a system of addressable remote electrodes that stimulate body tissue without requiring a main body to send commands for individual stimulations. The remote electrodes are specified to be of a size and shape suitable for injection rather than for endocardial implantation. A controller sets operating parameters and sends the parameters to remote electrodes by addressable communication, enabling the remote electrodes to function relatively autonomously while incurring some overhead to controller operations. However, the remote electrodes do not sense or monitor cardiac information and rely on the main body to provide sensing functionality. In contrast, the illustrative leadless pacemaker 102 combines pacing and sensing of intrinsic cardiac activity in a single implantable body.

Also shown in FIG. 2, a cylindrical hermetic housing 110 is shown with annular electrodes 108 at housing extremities. In the illustrative embodiment, the housing 110 can be composed of alumina ceramic which provides insulation between the electrodes. The electrodes 108 are deposited on the ceramic, and are platinum or platinum-iridium.

Several techniques and structures can be used for attaching the housing 110 to the interior or exterior wall of cardiac muscle 104.

A helix 226 and slot 228 enable insertion of the device endocardially or epicardially through a guiding catheter. A screwdriver stylet can be used to rotate the housing 110 and force the helix 226 into muscle 104, thus affixing the electrode 108A in contact with stimulable tissue. Electrode 108B serves as an indifferent electrode for sensing and pacing. The helix 226 may be coated for electrical insulation, and a steroid-eluting matrix may be included near the helix to minimize fibrotic reaction, as is known in conventional pacing electrode-leads.

In other configurations, suture holes 224 and 225 can be used to affix the device directly to cardiac muscle with ligatures, during procedures where the exterior surface of the heart is exposed.

Other attachment structures used with conventional cardiac electrode-leads including tines or barbs for grasping trabeculae or other structures in the interior of the ventricle, atrium, or coronary sinus may also be used in conjunction with or instead of the illustrative attachment structures.

Referring to FIG. 3, a pictorial view shows another embodiment of a pulse generator that includes a cylindrical metal housing 310 with an annular electrode 108A and a second electrode 108B. Housing 310 can be constructed from titanium or stainless steel. Electrode 108A can be constructed using a platinum or platinum-iridium wire and a ceramic or glass feed-thru to provide electrical isolation from the metal housing. The housing can be coated with a biocompatible polymer such as medical grade silicone or polyurethane except for the region outlined by electrode 108B. The distance between electrodes 108A and 108B should be approximately 1 cm to optimize sensing amplitudes and pacing thresholds. A helix 226 and slot 228 can be used for insertion of the device endocardially or epicardially through a guiding catheter. In addition, suture sleeves 302 and 303 made from silicone can be used to affix to the device directly to cardiac muscle with ligatures.

Figure 4:
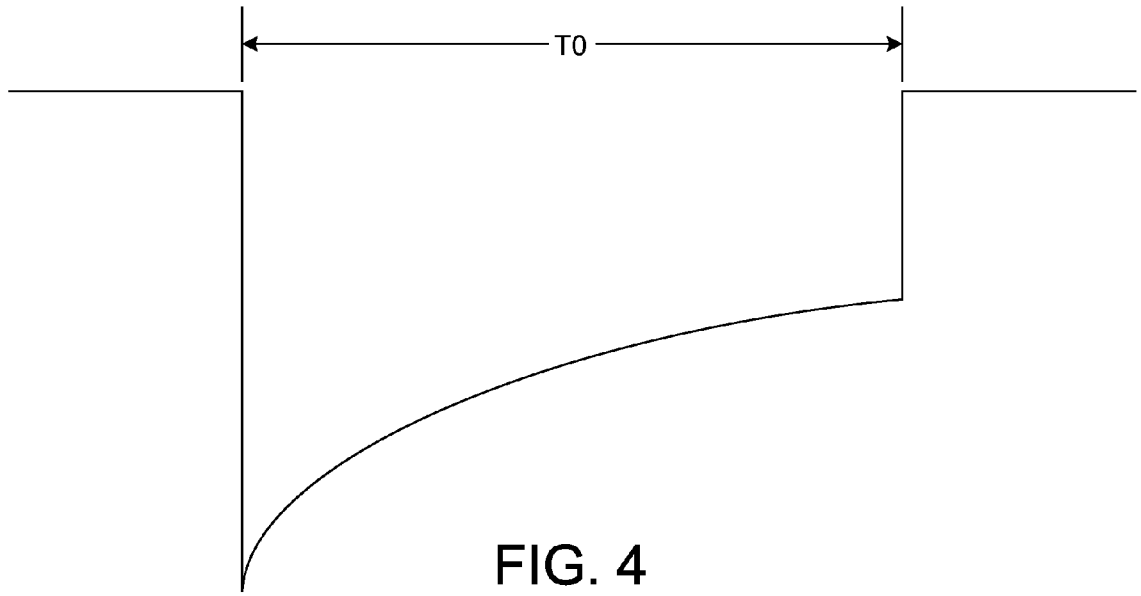
FIG. 4 is a time waveform graph illustrating a conventional pacing pulse.

Referring to FIG. 4, a typical output-pulse waveform for a conventional pacemaker is shown. The approximately-exponential decay is due to discharge of a capacitor in the pacemaker through the approximately-resistive load presented by the electrode/tissue interface and leads. Typically the generator output is capacitor-coupled to one electrode to ensure net charge balance. The pulse duration is shown as T0 and is typically 500 microseconds.

When the depicted pacemaker 102 is providing a pacing pulse but is not optionally sending data for communication, the pacing waveform of the pacemaker 102 can also resemble the conventional pacing pulse shown in FIG. 4.

Figure 5:
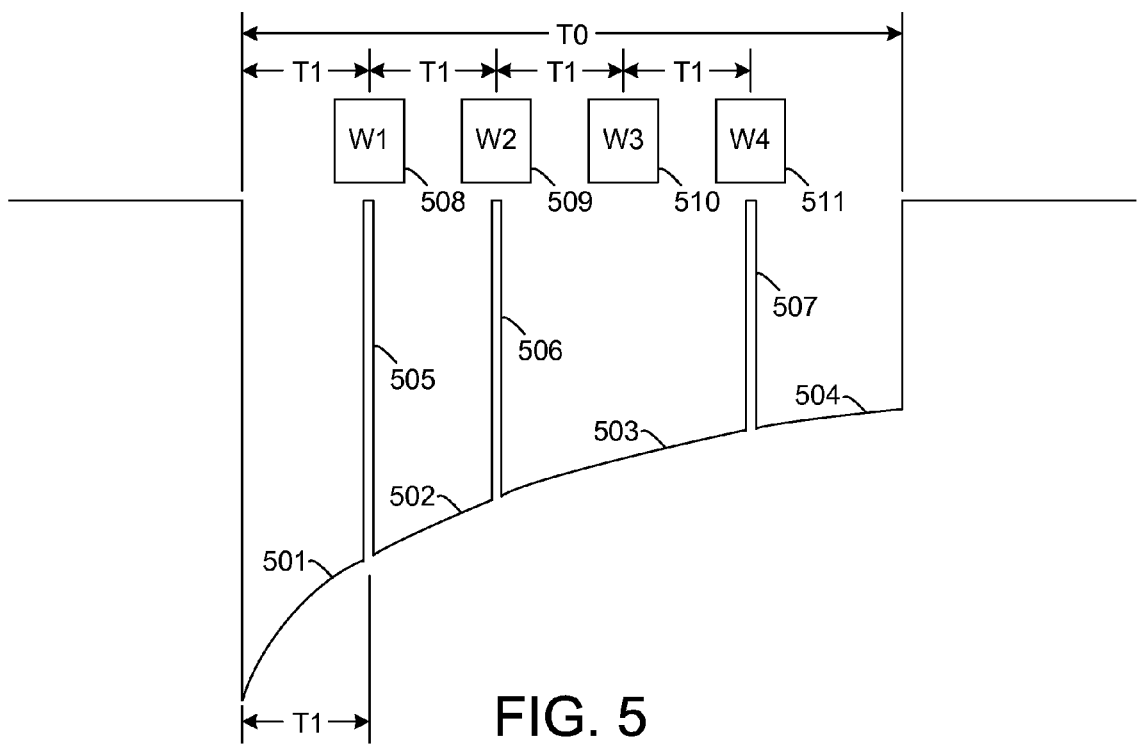
FIG. 5 is a time waveform graph depicting a pacing pulse adapted for communication as implemented for an embodiment of the illustrative pacing system.

Referring to FIG. 5, a time waveform graph depicts an embodiment of an output-pacing pulse waveform adapted for communication. The output-pulse waveform of the illustrative leadless pacemaker 102 is shown during a time when the pacemaker 102 is optionally sending data for communication and also delivering a pacing pulse, using the same pulse generator 116 and electrodes 108 for both functions.

FIG. 5 shows that the pulse generator 102 has divided the output pulse into shorter pulses 501, 502, 503, 504; separated by notches 505, 506, and 507. The pulse generator 102 times the notches 505, 506, and 507 to fall in timing windows W1, W2, and W4 designated 508, 509, and 511 respectively. Note that the pacemaker 102 does not form a notch in timing window W3 designated 510. The timing windows are each shown separated by a time T1, approximately 100 microseconds in the example.

As controlled by processor 112, pulse generator 116 selectively generates or does not generate a notch in each timing window 508, 509, 510, and 511 so that the device 102 encodes four bits of information in the pacing pulse. A similar scheme with more or fewer timing windows can send more or fewer bits per pacing pulse. The width of the notches is small, for example approximately 15 microseconds, so that the delivered charge and overall pulse width, specifically the sum of the widths of the shorter pulses, in the pacing pulse is substantially unchanged from that shown in FIG. 4. Accordingly, the pulse shown in FIG. 5 can have approximately the same pacing effectiveness as that shown in FIG. 4, according to the law of Lapique which is well known in the art of electrical stimulation.

In a leadless cardiac pacemaker, a technique can be used to conserve power when detecting information carried on pacing pulses from other implanted devices. The leadless cardiac pacemaker can have a receiving amplifier that implements multiple gain settings and uses a low-gain setting for normal operation. The low-gain setting could be insufficiently sensitive to decode gated information on a pacing pulse accurately but could detect whether the pacing pulse is present. If an edge of a pacing pulse is detected during low-gain operation, the amplifier can be switched quickly to the high-gain setting, enabling the detailed encoded data to be detected and decoded accurately. Once the pacing pulse has ended, the receiving amplifier can be set back to the low-gain setting. For usage in the decoding operation, the receiving amplifier is configured to shift to the more accurate high-gain setting quickly when activated. Encoded data can be placed at the end of the pacing pulse to allow a maximum amount of time to invoke the high-gain setting.

Figure 6:
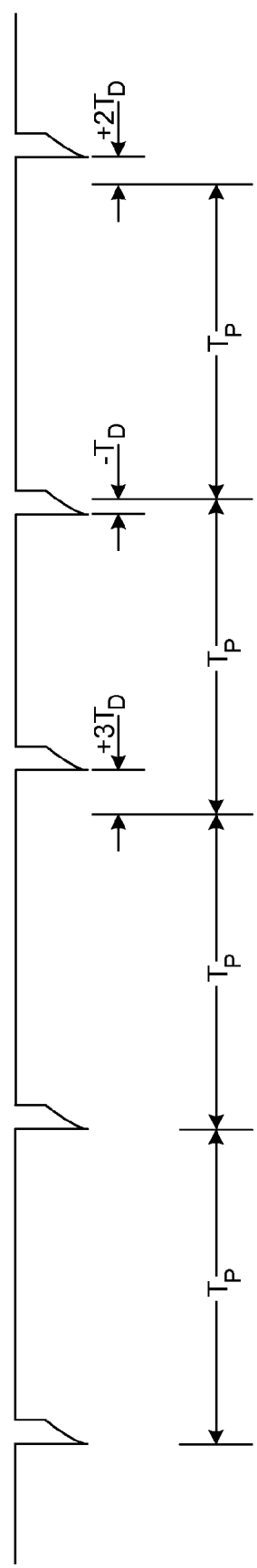
FIG. 6 is a time waveform graph depicting a pacing pulse adapted for communication using off-time variation as implemented for an embodiment of the illustrative pacing system.

Alternatively or in addition to the use of notches in the stimulation pulse for encoding and transmitting information, the pulses can have varying off-times, for instance times between pulses during which no stimulation occurs. Varying off-times can be small, for example less than 10 milliseconds total or any suitable duration, and can impart information based on the difference between a specific pulse's off-time and a preprogrammed off-time based on desired heart rate. For example, the device could impart four bits of information with each pulse by defining 16 off-times centered around the preprogrammed off-time. FIG. 6 is a graph that shows an example embodiment of a sample pulse generator output which incorporates the varying off-time scheme. Time $T_P$ represents the preprogrammed pulse timing. Time $T_d$ is a delta time associated with a single bit resolution for the data sent by the pulse generator. The number of $T_d$ time increments before or after the moment specified by $T_P$ gives the specific data element transmitted. The receiver of the pulse generator's communication has information relating to the pulse timing $T_P$ in advance. The communication scheme is most useful in applications of overdrive pacing in which pulse timing $T_P$ is not changing or altered by detected beats.

FIG. 5 depicts a technique in which information is encoded in notches in the pacing pulse. FIG. 6 shows a technique of conveying information by modulating the off-time between pacing pulses. Alternatively or in addition to the two illustrative coding schemes, overall pacing pulse width can be used to impart information. For example, a paced atrial beat may exhibit a pulse width of 500 microseconds and an intrinsic atrial contraction can be identified by reducing the pulse width by 30 microseconds. Information can be encoded by the absolute pacing pulse width or relative shift in pulse width. Variations in pacing pulse width can be relatively small and have no impact on pacing effectiveness.

To ensure the leadless cardiac pacemaker functions correctly, a specific minimum internal supply voltage is maintained. When pacing tank capacitor charging occurs, the supply voltage can drop from a pre-charging level which can become more significant when the battery nears an end-of-life condition and has reduced current sourcing capability. Therefore, a leadless cardiac pacemaker can be constructed with a capability to stop charging the pacing tank capacitor when the supply voltage drops below a specified level. When charging ceases, the supply voltage returns to the value prior to the beginning of tank capacitor charging.

In another technique, the charge current can be lowered to prevent the supply voltage from dropping below the specified level. However, lowering the charge current can create difficulty in ensuring pacing rate or pacing pulse amplitude are maintained, since the lower charge current can extend the time for the pacing tank capacitor to reach a target voltage level.

The schemes for transmitting data do not significantly increase the current consumption of the pacemaker disclosed herein. For example, the pacemaker could transmit data continuously in a loop with no consumption penalty.

Referring again to FIG. 1B, the circuit 134 for receiving communication via electrodes 108 is shown. The communication can be coded with a pulse-position scheme as illustrated by FIG. 5 for the signal sent from the pacemaker, or can otherwise be a pulse-modulated or frequency-modulated carrier signal, for example in a range from 10 kHz to 100 kHz. A pacing pulse of 5 volts and 5 milliamps amplitude with duration of 500 microseconds and a period of 500 milliseconds corresponds to a power consumption of 25 microwatts.

In a pacemaker 102, the processor 112 typically includes a timer with a slow clock with a suitable period, for example approximately 10 milliseconds, and an instruction-execution clock with a suitable period, for example approximately one microsecond. The processor 112 typically operates the instruction-execution clock only briefly in response to events originating with the timer, the communication amplifier 134, or cardiac sensing amplifier 132. At other times, only the slow clock and timer operate so that the power consumption specification of the processor 112 is no more than 5 microwatts.

For a pacemaker that operates with the aforementioned slow clock, the instantaneous power consumption specification, even for a commercially-available micropower microprocessor, would exceed the battery's power capabilities and would require an additional filter capacitor across the battery to prevent a drop of battery voltage below the voltage necessary to operate the circuit. The filter capacitor would add avoidable cost, volume, and potentially lower reliability.

For example, a microprocessor consuming only 100 microamps would require a filter capacitor of 5 microfarads to maintain a voltage drop of less than 0.1 volt, even if the processor operates for only 5 milliseconds. To avoid the necessity for such a filter capacitor, an illustrative embodiment of a processor can operate from a lower frequency clock to avoid the high instantaneous power consumption, or the processor can be implemented using dedicated hardware state machines to supply a lower instantaneous peak power specification.

In a pacemaker 102, the cardiac sensing amplifier operates with a power consumption of no more than 5 microwatts. A communication amplifier that operates at a suitable frequency for usage in an implantable device, for example approximately 100 kHz, has a power consumption of no more than 25 microwatts in some embodiments. The battery ammeter 136 and battery voltmeter 138 operate at a power consumption of no more than 1 microwatt each. The pulse generator 116 typically includes an independent rate limiter with a power consumption of no more than 2 microwatts.

In conventional implantable devices, a communication amplifier and a sensing amplifier both continuously consume power, for example constantly requiring on the order of 25 microwatts and 5 microwatts respectively from the battery. In some embodiments of the implantable biostimulator described herein, operation of the communications amplifier and charging of the pacing tank capacitor can be made mutually exclusive. For example, after the pacing pulse, charging of the pacing tank capacitor can be suspended by an appropriate time window, for example 10 milliseconds. During the window, the communication amplifier can be enabled and ready to receive commands and information from an external programmer or another implantable device. Thus, the 25 microwatts used by the communications amplifier is mutually exclusive from the 25 microwatts consumed by charging the pacing tank capacitor, enabling the total power consumption of the biostimulator to drop to 39 microwatts.

The total power consumption of the pacemaker is thus 64 microwatts, less than the disclosed 70-microwatt battery output.

Improvement attained by the illustrative cardiac pacing system 100 and cardiac pacemaker 102 is apparent.

The illustrative cardiac pacing system 100 enables encoding outgoing communication in the pacing pulse, so that the total power consumption for outgoing communication and pacing does not exceed the power consumption for pacing alone. Thus, the power consumption for outgoing communication is effectively zero because outgoing communication uses the same power already used to create a pacing pulse.

The illustrative cardiac pacemaker 102 can have sensing and processing circuitry that consumes no more than 25 microwatts as in conventional pacemakers.

The described leadless cardiac pacemaker 102 can have an incoming communication amplifier for receiving communication which consumes no more than 25 microwatts.

Furthermore, the cardiac pacemaker 102 can have a primary battery, for example a beta-voltaic primary battery that produces sufficient power, for example 100 microwatts, in a suitably compact volume, for example less than one cubic centimeter. In addition, the leadless cardiac pacemaker 102 can have a primary battery that exhibits an energy density of at least 3 W·h/cc.

Terms "substantially", "essentially", or "approximately", that may be used herein, relate to an industry-accepted tolerance to the corresponding term. Such an industry-accepted tolerance ranges from less than one percent to twenty percent and corresponds to, but is not limited to, component values, integrated circuit process variations, temperature variations, rise and fall times, and/or thermal noise. The term "coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. Inferred coupling, for example where one element is coupled to another element by inference, includes direct and indirect coupling between two elements in the same manner as "coupled".

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims. Variations and modifications of the embodiments disclosed herein may also be made while remaining within the scope of the following claims. For example, although the description has some focus on pacemakers; systems, structures, and techniques can otherwise be applicable to other uses, for example multi-site pacing for prevention of tachycardias in the atria or ventricles. Phraseology and terminology employed herein are for the purpose of the description and should not be regarded as limiting. With respect to the description, optimum dimensional relationships for the component parts are to include variations in size, materials, shape, form, function and manner of operation, assembly and use that are deemed readily apparent and obvious to one of ordinary skill in the art and all equivalent relationships to those illustrated in the drawings and described in the specification are intended to be encompassed by the present description. Therefore, the foregoing is considered as illustrative only of the principles of structure and operation. Numerous modifications and changes will readily occur to those of ordinary skill in the art whereby the scope is not limited to the exact construction and operation shown and described, and accordingly, all suitable modifications and equivalents may be included.

What is claimed is:

1. A leadless biostimulator comprising:
a housing;
a plurality of electrodes formed integrally to the housing or coupled to the housing and separated by a maximum distance of 2 centimeters from the housing;
a pulse generator hermetically contained within the housing and electrically coupled to the electrode plurality, the pulse generator configured to generate and deliver electrical pulses via the electrode plurality;
a processor hermetically contained within the housing and communicatively coupled to the pulse generator and the electrode plurality, the processor being configured to control electrical pulse delivery according to programmed instructions; and a power supply hermetically contained within the housing and coupled to the pulse generator, the power supply configured to supply energy for operations and electrical pulse generation as a source internal to the housing, the power supply further comprising a primary battery that has a volume less than approximately 1 cubic centimeter and sources sufficient energy for supporting circuitry that consumes a maximum of 64 microwatts, wherein the pulse generator is further configured to selectively generate and deliver electrical energy in a stimulation pulse to at least two of the electrode plurality for causing a contraction of a patient's heart in response to control signals from the processor, the stimulation pulse being interrupted by at least one notch configured to convey information to a device external to the biostimulator.

2. The biostimulator according to claim 1, wherein the processor is further configured to communicate control signals to the pulse generator specifying characteristics of the at least one notch and defining the conveyed information.

3. The biostimulator according to claim 1, wherein the conveyed information comprises data selected from a group consisting of programmable parameter settings, event counts, power-supply voltage, and power-supply current.

4. The biostimulator according to claim 1, wherein a width of the at least one notch is approximately 15 microseconds.

5. The biostimulator according to claim 1, wherein the at least one notch occurs in at least one timing window.

6. The biostimulator according to claim 1, wherein the at least one notch occurs in at least one timing window and spacing between timing windows is approximately 100 microseconds.

7. The biostimulator according to claim 1, wherein the power supply further comprises a primary battery formed of a beta-voltaic converter configured to obtain electrical energy from radioactivity.

8. The biostimulator according to claim 1 further comprising:
a regulator circuit electrically connected between the power supply and biostimulator circuitry, the regulator circuit configured to regulate voltage supply for powering biostimulator circuitry.

9. The biostimulator according to claim 1, wherein the power supply further comprises a primary battery, and wherein the biostimulator further comprises a battery ammeter in the power supply configured for indicating battery current drain and indirect device health for usage by the processor.

10. The biostimulator according to claim 1, wherein the power supply further comprises a primary battery, and wherein the biostimulator further comprises a battery voltmeter in the power supply configured for indicating battery voltage for usage by the processor.

11. The biostimulator according to claim 1 further comprising:
a tissue connector adapted to affix the housing to cardiac muscle, the tissue connector selected from a group consisting of a helix configured to rotatably advance into the cardiac muscle, at least one member pierced with a hole for passing a suture, and at least one tine.

12. The biostimulator according to claim 1 wherein:
the housing is cylindrical; and
the electrode plurality comprises annular electrodes located at extremities of the housing.

13. The biostimulator according to claim 1 wherein:
the housing is constructed from a ceramic material; and
the electrode plurality is deposited on the ceramic material.

14. The biostimulator according to claim 1 wherein:
the housing is operative as an electrode and constructed from titanium or stainless steel and is coated over part of an exterior surface with a silicone rubber or polyurethane insulating material.

15. The biostimulator according to claim 1 wherein:
the biostimulator is a leadless cardiac pacemaker.

16. A leadless biostimulator comprising:
a housing;
a plurality of electrodes formed integrally to the housing or coupled to the housing and separated by a maximum distance of 2 centimeters from the housing;
a pulse generator hermetically contained within the housing and electrically coupled to the electrode plurality, the pulse generator configured to generate and deliver electrical pulses via the electrode plurality;
a processor hermetically contained within the housing and communicatively coupled to the pulse generator and the electrode plurality, the processor being configured to control electrical pulse delivery according to programmed instructions; and
a power supply hermetically contained within the housing and coupled to the pulse generator, the power supply configured to supply energy for operations and electrical pulse generation as a source internal to the housing, the power supply further comprising a primary battery that has a volume less than approximately 1 cubic centimeter and sources sufficient energy for supporting circuitry that consumes a maximum of 64 microwatts, wherein the pulse generator is further configured to selectively generate and deliver electrical energy in a stimulation pulse to at least two of the electrode plurality for causing a contraction of a patient's heart in response to control signals from the processor, wherein the pulse generator is further configured to generate and deliver electrical energy in a series of stimulation pulses with time between the stimulation pulses selectively varied to convey information to a device external to the biostimulator.

17. The biostimulator according to claim 16 wherein:
the variation of time between pulses is less than a total of 10 milliseconds.

18. A leadless biostimulator comprising:
a housing;
a plurality of electrodes formed integrally to the housing or coupled to the housing and separated by a maximum distance of 2 centimeters from the housing;
a pulse generator hermetically contained within the housing and electrically coupled to the electrode plurality, the pulse generator configured to generate and deliver electrical pulses via the electrode plurality;
a processor hermetically contained within the housing and communicatively coupled to the pulse generator and the electrode plurality, the processor being configured to control electrical pulse delivery according to programmed instructions; and
a power supply hermetically contained within the housing and coupled to the pulse generator, the power supply configured to supply energy for operations and electrical pulse generation as a source internal to the housing, the power supply further comprising a primary battery that has a volume less than approximately 1 cubic centimeter and sources sufficient energy for supporting circuitry that consumes a maximum of 64 microwatts, wherein the pulse generator is configured to generate and deliver electrical energy in a series of stimulation pulses with pacing pulse width selectively varied to convey information to a device external to the biostimulator.

19. A leadless biostimulator comprising:
a housing;
a plurality of electrodes formed integrally to the housing or coupled to the housing and separated by a maximum distance of 2 centimeters from the housing;
a pulse generator hermetically contained within the housing and electrically coupled to the electrode plurality, the pulse generator configured to generate and deliver electrical pulses via the electrode plurality;
a processor hermetically contained within the housing and communicatively coupled to the pulse generator and the electrode plurality, the processor being configured to control electrical pulse delivery according to programmed instructions;
a power supply hermetically contained within the housing and coupled to the pulse generator, the power supply configured to supply energy for operations and electrical pulse generation as a source internal to the housing, the power supply further comprising a primary battery that has a volume less than approximately 1 cubic centimeter and sources sufficient energy for supporting circuitry that consumes a maximum of 64 microwatts;
a receiving amplifier/filter adapted for multiple controllable gain settings; and
a processor configured to control gain setting for the receiving amplifier/filter, invoking a low-gain setting for normal operation and detecting presence of an electrical pulse, and invoking a high-gain setting for detecting and decoding information encoded in the detected electrical pulse.

20. The system according to claim 19 further comprising:
a tank capacitor coupled across a pair of the electrode plurality and adapted for charging and discharging wherein an electrical pulse is generated;
a charge pump circuit coupled to the tank capacitor and adapted for controlling charging of the tank capacitor; and
a processor configured to control recharging of the tank capacitor wherein recharging is discontinued when a battery terminal voltage falls below a predetermined value to ensure sufficient voltage for powering the leadless biostimulator.

21. A leadless cardiac pacemaker comprising:
a housing;
a plurality of electrodes formed integrally to the housing or coupled to the housing and separated by a maximum distance of 2 centimeters from the housing;
a pulse generator hermetically contained within the housing and electrically coupled to the electrode plurality, the pulse generator configured for generating and delivering electrical pulses to the electrode plurality and causing cardiac contractions, the pulse generator further configured to convey information to at least one device external to the pacemaker by conductive communication encoded on pulses via the electrode plurality;
at least one amplifier hermetically contained within the housing and electrically coupled to the electrode plurality, the at least one amplifier configured to amplify signals received from the electrode plurality and to detect cardiac contractions, the at least one amplifier further configured to receive information from the at least one external device;
a processor hermetically contained within the housing and communicatively coupled to the pulse generator, the at least one amplifier, and the electrode plurality, the processor configured to receive amplifier output signals from the amplifier, control communications, and control electrical pulse delivery according to programmed instructions; and
a power supply hermetically contained within the housing and coupled to the pulse generator, the power supply configured to supply energy for operations, communication, and electrical pulse generation as a source internal to the housing.

22. The pacemaker according to claim 21 further comprising:
the pulse generator configured to consume a maximum electrical power of 27 microwatts averaged over one cardiac cycle.

23. The pacemaker according to claim 21 further comprising:
the amplifier configured to consume a maximum electrical power of 30 microwatts.

24. The pacemaker according to claim 21 further comprising:
the power supply configured to consume a maximum electrical power of 2 microwatts and configured to supply a minimum electrical power of approximately 64 microwatts.

25. The pacemaker according to claim 21 further comprising:
the processor configured to consume a maximum electrical power of 5 microwatts averaged over one cardiac cycle.

26. A leadless biostimulator comprising:
a housing;
a plurality of electrodes formed integrally to the housing or coupled to the housing and separated by a maximum distance of 2 centimeters from the housing;
a pulse generator hermetically contained within the housing and electrically coupled to the electrode plurality, the pulse generator configured for generating and delivering electrical pulses to the electrode plurality; and
a processor hermetically contained within the housing and communicatively coupled to the pulse generator and the electrode plurality, the processor configured to control electrical pulse delivery and configured to communicate with at least one device external to the biostimulator by conductive communication signals encoded on pulses via the electrode plurality.

27. The biostimulator according to claim 26 further comprising:
the processor being configured to control electrical pulse delivery according to at least one programmable parameter, the processor configured to be programmable by conducted communication signals transmitted via the electrode plurality.

28. The biostimulator according to claim 26 further comprising:
the processor being configured to communicate to the at least one device external to the biostimulator by communication signals transmitted via the electrode plurality.

29. The biostimulator according to claim 26 wherein:
the biostimulator is a leadless cardiac pacemaker.

* * * * *